US008906933B2

(12) United States Patent
Sun et al.

(10) Patent No.: US 8,906,933 B2
(45) Date of Patent: *Dec. 9, 2014

(54) DIHYDROPYRIMIDIN-2(1H)-ONE COMPOUNDS AS NEUROKININ-3 RECEPTOR ANTAGONISTS

(75) Inventors: Xicheng Sun, Broomfield, CO (US); Jian Qiu, Longmont, CO (US)

(73) Assignee: N30 Pharmaceuticals, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/814,316

(22) PCT Filed: Sep. 24, 2010

(86) PCT No.: PCT/US2010/050186
§ 371 (c)(1),
(2), (4) Date: Feb. 5, 2013

(87) PCT Pub. No.: WO2012/039718
PCT Pub. Date: Mar. 29, 2012

(65) Prior Publication Data
US 2013/0131093 A1    May 23, 2013

(51) Int. Cl.
| | | |
|---|---|---|
| *A61K 31/505* | (2006.01) | |
| *C07D 409/14* | (2006.01) | |
| *C07D 413/10* | (2006.01) | |
| *C07D 239/22* | (2006.01) | |
| *C07D 409/04* | (2006.01) | |

(52) U.S. Cl.
CPC ............ *C07D 239/22* (2013.01); *C07D 409/14* (2013.01); *C07D 413/10* (2013.01); *C07D 409/04* (2013.01); *A61K 31/505* (2013.01)
USPC ........................................................ 514/274

(58) Field of Classification Search
CPC .. C07D 241/06; C07D 211/22; C07D 211/76; C07D 239/34; C07D 239/36; A61K 31/495; A61K 31/505; A61K 31/515
See application file for complete search history.

(56) References Cited

U.S. PATENT DOCUMENTS

| | | | |
|---|---|---|---|
| 5,434,158 | A | 7/1995 | Shah |
| 6,268,369 | B1 | 7/2001 | Nagarathnam et al. |
| 7,566,723 | B2 | 7/2009 | Gielen-Haertwig et al. |
| 8,741,915 | B2 | 6/2014 | Sun et al. |
| 2002/0128205 | A1 | 9/2002 | Stamler et al. |
| 2005/0014697 | A1 | 1/2005 | Stamler et al. |
| 2005/0187166 | A1 | 8/2005 | Stamler et al. |
| 2009/0163545 | A1 | 6/2009 | Goldfarb |
| 2010/0286174 | A1 | 11/2010 | Stamler et al. |
| 2012/0208817 | A1 | 8/2012 | Sun et al. |
| 2013/0096161 | A1 | 4/2013 | Sun et al. |

FOREIGN PATENT DOCUMENTS

| | | |
|---|---|---|
| EP | 1439175 A1 | 7/2004 |
| JP | 2007001104 | 1/2007 |
| WO | WO 96/35677 | 11/1996 |
| WO | WO 99/65315 | 12/1999 |
| WO | WO 2004/009560 | 1/2004 |
| WO | WO 2004/101742 | 11/2004 |
| WO | WO 2006/097617 | 9/2006 |
| WO | WO 2006/131676 | 12/2006 |
| WO | WO 2007104034 | 9/2007 |
| WO | WO 2008/103068 | 8/2008 |
| WO | WO 2008/118391 | 10/2008 |
| WO | WO 2009/076665 | 6/2009 |
| WO | WO 2009/150668 A1 * | 12/2009 |
| WO | WO 2010019910 | 2/2010 |
| WO | WO 2010/046780 | 4/2010 |
| WO | WO 2010/107476 | 9/2010 |
| WO | WO 2011/038204 | 3/2011 |
| WO | WO 2012/009227 | 1/2012 |

OTHER PUBLICATIONS

Albert et al ("Neurokinin-3 receptor antagonists in schizophrenia." Exprt Opin. Ther. Patents, 2006; 16(7):925-937).*
Meltzer et al ("NK3 receptor antagonists for the treatment of schizophrenia", Drug Discovery Today: Therapeutic Strategies, 2006; 3(4):555-560).*
Harris et al (Irritable Bowel Syndrome and Chronic Constipation: Emerging Drugs, Devices, and Surgical Treatments, Current Gastroenterology Reports, 2006; 8:282-290).*
Bruno et al. (1993) "3,5-diphenyl-1H-pyrazole derivatives. XI. N-aryl-5(3)-phenyl-4-(3,5-diphenyl-1-pyrazolyl)-3(5)-pyrazole amines, 5-substituted 4,5-dihydro-3-phenyl- 4-(3,5-diphenyl-1-pyrazolyl)-1H-pyrazoles and 2,6-disubstituted 1,6-dihydro-4-phenyl-5-(3,5-diphenyl-1-pyrazolyl)pyrimidines with antipyretic, antiinflammatory and other activities." Il Farmaco 48(7):949-966.
Akbar et al. (2009) Aliment Pharmaco Ther. 30:423-435, "Review article: visceral hypersensitivity in irritable bowel syndrome: molecular mechanisms and therapeutic agents".
Blaney et al. (2001) "Stepwise Modulation of Neurokinin-3 and Neurokinin-2 Receptor Affinity and Selectivity in Quinoline Tachykinin Receptor Antagonists", J. Med. Chem., 44(11):1675-1689.
Bueno et al. (2002) Gut 51: i19-i23: doi: 10.1136/gut.51.suppl_1.i19 "Visceral perception: inflammatory and non-inflammatory mediators".
Chemical Abstracts Service, Columbus, Ohio, US; Aug. 21, 2004 (Aug. 21, 2004), XP002690644, retrieved from STN—Registry No. 729560-89-8 abstract Database Registry [Online].
Chemical Abstracts Service, Columbus, Ohio, US; Jan. 4, 2002 (Jan. 4, 2002), XP002690645, retrieved from STN—Registry No. 380467-43-6 abstract Database Registry [Online].
Chemical Abstracts Service, Columbus, Ohio, US; Mar. 14, 2001 (Mar. 14, 2001), XP002690646, retrieved from STN—Registry No. 327091-97-4 abstract Database Registry [Online].
Chemical Abstracts Service, Columbus, Ohio, US; Mar. 7, 2001 (Mar. 7, 2001), XP002690647—retrieved from STN—Registry No. 326024-49-1 Registry numbers: 326024-49-1, 326010-63-3 and 326010-60-0 Database Registry [Online].

(Continued)

*Primary Examiner* — Marcos Sznaidman
*Assistant Examiner* — Rayna B Rodriguez
(74) *Attorney, Agent, or Firm* — Swanson & Bratschun, L.L.C.

(57) ABSTRACT

The present invention is directed to novel dihydropyrimidin-2(1H)-one compounds useful as Neurokinin-3 (NK3) receptor antagonists, pharmaceutical compositions comprising such compounds, and methods of making and using the same.

10 Claims, No Drawings

(56) References Cited

OTHER PUBLICATIONS

Chemical Abstracts Service. Columbus, Ohio. US; Mar. 6, 2001 (Mar. 6, 2001). XP002690648, retrieved from STN—Registry No. 325823-34-5 abstract Database Registry [Online].
Chemical Abstracts Service. Columbus, Ohio. US; Mar. 5, 2001 (Mar. 5, 2001) XP002690649 retrieved from STN—Registry No. 325763-84-6 CAS Registry Nos. 325763-84-6. 325751-72-2 and 325749-34-6.
de Belder et al. (May 1994) "Effects of S-nitroso-glutathione in the human forearm circulation; evidence for selective inhibition of platelet activation", *Cardiovasc Res.*, 28(5):691-694.
de Jesus-Berrios et al. (Nov. 2003) "Enzymes that Counteract Nitrosative Stress Promot Fungal Virulence", *Curr. Biol.*, 13:1963-1968.
Dzvinchuk, I. B. et al. (2002) "2-phenacylbenzothiazole in the Biginelli reaction", *Chemistry of Heterocyclic Compounds*, 38(8), 1000-1007.
Dzvinchuk, I. B. et al. (2003) "2-Acylmethyl-1H-benzimidazoles in the Biginelli reaction", *Chemistry of Heterocyclic Compounds*, 39(4), 455-460.
European Search Report issued Feb. 20, 2013 in European Patent Application Serial No. 10819517.3.
Foster et al. (Apr. 2003) "S-nitrosylation in health and disease", *Trends in Molecular Medicine*, 9(4):160-168.
Gaston et al. (Dec. 1993) "Endogenous nitrogen oxides and bronchodilator S-nitrosolthiols in human airways", *Proc. Natl. Acad. Sci. USA*, 90:10957-10961.
International Preliminary Report on Patentability issued in PCT/US2010/050164 mailed Apr. 5, 2012.
International Preliminary Report on Patentability issued in PCT/US2010/050186 issued Mar. 26, 2013.
International Search Report and Written Opinion issued in PCT/US2010/050164 mailed Nov. 15, 2010.
International Search Report and Written Opinion issued in PCT/US2010/050186 mailed Nov. 18, 2010.
Jensen et al. (1998) "S-Nitrosoglutathione is a substrate for rat alcohol dehydrognease class III isoenzyme", *Biochem J.*, 331:659-668.
Kaposzta et al. (2002) "S-Nitrosoglutathione Reduces Asymptomatic Embolization After Carotid Angioplasty", *Circulation*,106(24):3057-3062.
Kefayati et al. (2009) "An efficient synthesis of new 3,4-dihydropyrimidin-2(1H)-ones incorporating a phenyl moiety at C-5 and C-6 catalyzed by TMSCl and Co(OAc)2.4H2O" *Phosphorus, Sulfur and Silicon and the Related Elements*, 184(7), 1796-1804.
Lipton et al. (Sep. 2001) "S-Nitrosothiols signal the ventilatory response to hypoxia", *Nature*, 413:171-174.

Liu et al. (Mar. 2001) "A metabolic enzyme for S-nitrosothiol conserved from bacterial to humans", *Nature*, 410:490-494.
Liu et al. (Feb. 2004) "Essential Roles of S-Nitrosothiols in Vascular Homeostatsis and Endotoxic Shock", *Cell*, 116(4):617-628.
Maggio (1988) Ann. Rev. Neurosci. 11:13-28, "Tachykinins".
Que et al. (Jun. 2005) "Protection from Experimental Asthma by an Endogenous Bronchodilator", *Science*, 308(5728):1618-1621.
Malherbe et al. (2009) "Identification of a Critical Residue in the Transmembrane Domain 2 of Tachykinin Neurokinin 3 Receptor Affecting the Dissociation Kinetics and Antagonism Mode of Osanetant (SR 142801) and Piperidine-Based Structures", Journal of Medicinal Chemistry 52:7103-7112.
Sanger (2004) British Journal of Pharmacology 141:1303-1312, "Neurokin NK1 and NK3 receptors as targets for drugs to treat gastrointestinal motility disorders and pain".
Sanghani et al. (2000) "Kinetic Mechanism of Human Glutathioone-Dependent Formaldehyde Dehydrogenase", *Biochemistry*, 39:10720-10729.
Sanghani et al. (2002) "Human Glutathione-Dependent Formaldehyde Dehydrognease. Structures of Apo, Binary, and Inhibitory Ternary Complexes", *Biochemistry*,41:10778-10786.
Shen et al. (2010) "Bronsted Base-Catalyzed One-Pot Three-Component Biginelli-Type Reaction: An Efficient Synthesis of 4,5,6-Triaryl-3,4-dihydropyrimidin-2(1H)-one and Mechanistic Study" Journal of Organic Chemistry, 75(4), 1162-1167.
Spooren et al. (Dec. 2005) Nature Reviews 4:967-975, "NK3 receptor antagonists: the next generation of antipsychotics?".
Staab et al. (2008) "Dual functions of alcohol dehydrogenase 3: implications with focus on formaldehyde dehydrogenase and S-nitroglutathione reductase activities", *Cell Mol. Life Sci*, 65:3950-3960.
Staab et al. (Jun. 15, 2009) "Medium-chain fatty acids and glutathione derivatives as inhibitors of S-nitrosoglutathione reduction mediated by alcohol dehydrogenase 3", Chemico-Biological Interactions 180(1):113-118.
Stamler et al. (Aug. 1992) "Nitric oxide circulates in mammalian plasma primarily as an S-nitrose adduct of serium albumin", *Proc. Natl. Acad. Sci. USA*, 89:7674-7677.
Uotila and Koivusalo (1989) Coenzymes and Cofactors vol. 3: Glutathione, part A., D. Dolphin, ed. pp. 517-551 (New York, John Wiley & Sons).
Zaman et al. (2001) "S-Nitrosoglutathione Increases Cystic Fibrosis Transmembrane Regulator Maturation", *Biochem Biophys Res Commun.*, 284:65-70.
European Search Report issued Mar. 19, 2014 in European Patent Application Serial No. 10857614.1.

\* cited by examiner

DIHYDROPYRIMIDIN-2(1H)-ONE COMPOUNDS AS NEUROKININ-3 RECEPTOR ANTAGONISTS

RELATED APPLICATIONS

This application is a 35 U.S.C. §371 national phase application of PCT/US2010/050186, filed Sep. 24, 2010 (WO 2012/039718), entitled "Novel Dihydropyrimidin-2(1H)-One Compounds As Neurokinin-3 Receptor Antagonists."

FIELD OF THE INVENTION

The present invention is directed to novel dihydropyrimidin-2(1H)-one compounds and pharmaceutical compositions comprising such compounds useful as antagonists of the Neurokinin-3 (NK3) receptor.

BACKGROUND

The mammalian tachykinins, also known as neurokinins, are a family of small peptides that share a common carboxyl-terminal sequence of Phe-X-Gly-Leu-Met-$NH_2$ (Maggio et al., *Annual Rev. Neuroscience* 11:13-28 (1998). The main members of the family are substance P (SP), neurokinin A (NKA) and neurokinin B (NKB). As neurotransmitters these peptides exert their biological activity via three distinct neurokinin (NK) receptors termed neurokinin-1 (NK1), neurokinin-2 (NK2) and neurokinin-3 (NK3). SP binds preferentially to NK1, NKA to NK2 and NKB to NK3. The NK3 receptor is characterized by a predominant expression in the central nervous system (CNS) and its involvement in the modulation of the central monoaminergic (noradenaline and dopamine) and amino acid (GABA) neurotransmission. These properties make the NK3 receptor a potential target for CNS diseases such as schizophrenia (Spooren et al., *Nat. Rev. Drug Discov.* 4:967-975 (2005).

Schizophrenia is a chronic, severe, and disabling brain disorder that affects about 1% of the world's population. Symptoms begin in early adulthood and are followed by a period of interpersonal and social dysfunction. The symptoms of schizophrenia fall into three broad categories: positive symptoms, negative symptoms, and cognitive symptoms. Positive symptoms include hallucinations, delusions, thought disorders and movement disorders. Negative symptoms include depression, anhedonia, blunted affect, diminished speech and cognitive symptoms include memory and attention deficits as well as social withdrawal.

There is no single cause of schizophrenia however, increased dopamine activity in the mesolimbic pathway of the brain is consistently found in schizophrenic individuals. The lack of knowledge about the exact cause and nature of this disease make development of new drugs difficult. Treatment has been focused on antipsychotic medication which primarily works by suppressing dopamine activity. As these drugs have evolved through the years the side effect profile has improved but they still exhibit some side effects such as weight gain. In 2004 Sanofi-Synthelabo published clinical results for Osanetant which was identified as a potent and selective antagonist of the NK3 receptor for the treatment of schizophrenia and in 2005 GSK published clinical results for talenant which was shown to ameliorate the cognitive issues of schizophrenics however, both compounds have poor pharmacokinetics and pharmacodynamic properties including poor solubility, poor bioavailability, relatively high clearance and poor brain-blood barrier penetration. In spite of the liabilities with these compounds, clinical results to date suggest that the NK3 receptor may prove to be a promising target for treatment of schizophrenia providing that pharmacokinetic and pharmacodynamic issues can be resolved.

Irritable bowel syndrome (IBS) is a chronic, episodic functional gastrointestinal (GI) disorder characterized by abdominal pain/discomfort and altered bowel habit (constipation, diarrhea or alternating periods of both). Patients often experience additional symptoms such as bloating, sensation of incomplete evacuation, straining (constipation) and urgency (diarrhea). IBS patients can experience symptoms for many years, with an average duration of 10 or more years. IBS is often unrecognized or untreated, with as few as 25% of IBS sufferers seeking professional health care. IBS prevalence is estimated to be up to 20% of the population. Functional bowel disorders such as IBS are characterized by visceral hypersensitivity defined by reduced pain and discomfort thresholds, which may manifest as pain associated with bowel disturbances (Akbar et al., *Alimentary Pharmacology and Therapeutics*, 30(5): 423-435 (2009). Although the pathogenesis of visceral hypersensitivity is not fully understood, several mechanisms have been proposed including subtle inflammation, psychosocial factors and altered sensorimotor function of the gut, a major component of which is believed to be peripheral and central sensitization of visceral afferent neuronal pathways. Similarly, the other functional bowel disorders such as noncardiac chest pain, functional dyspepsia and functional abdominal pain present commonly and treatment of these disorders can be challenging. Over the past 30 years, the main treatment of irritable bowel syndrome has aimed to normalize gastrointestinal transit using either laxatives or antidiarrheal agents, with or without the concurrent use of spasmolytics. These therapeutic options are limited and often disappointing in efficacy.

Recent investigation into the pathophysiology of irritable bowel syndrome has focused on evaluation of visceral hypersensitivity (Bueno et al. *Gut*, 51 (Suppl):19-23 (2002). At the same time, more information has been acquired on the status of the local immune system as a possible cause for sensitization of nerve terminals. Such investigations have stimulated the emergence of new concepts and original candidate drugs for the treatment of this functional disorder.

Tachykinin receptors do not appear to play significant roles in normal GI functions, but may be involved in defensive or pathological processes. NK3 receptors have been found to mediate certain disruptions of intestinal motility. The activity may be driven by tachykinins released from intrinsic primary afferent neurones (IPANs), which induce slow excitatory postsynaptic potential (EPSP) activity in connecting IPANs and hence, a degree of hypersensitivity within the enteric nervous system. The same process is also proposed to increase C-fibre sensitivity, either indirectly or directly. Thus, NK3 receptor antagonists inhibit intestinal nociception via a "peripheral" mechanism that may be intestine-specific. Studies with talnetant and other selective NK3 receptor antagonists revealed an exciting and novel pathway by which pathological changes in intestinal motility and nociception can be induced, suggesting a role for NK3 receptor antagonism in irritable bowel syndrome (Sanger, *Brit. J. of Pharm.*, 141: 1303-1312 (2004)).

The chemical compound nitric oxide is a gas with chemical formula NO. NO is one of the few gaseous signaling molecules known in biological systems, and plays an important role in controlling various biological events. For example, the endothelium uses NO to signal surrounding smooth muscle in the walls of arterioles to relax, resulting in vasodilation and increased blood flow to hypoxic tissues. NO is also involved in regulating smooth muscle proliferation, platelet function, neurotransmission, and plays a role in host defense. Although nitric oxide is highly reactive and has a lifetime of a few seconds, it can both diffuse freely across membranes and bind to many molecular targets. These attributes make NO an ideal signaling molecule capable of controlling biological events between adjacent cells and within cells.

NO is a free radical gas, which makes it reactive and unstable, thus NO is short lived in vivo, having a half life of 3-5 seconds under physiologic conditions. In the presence of oxygen, NO can combine with thiols to generate a biologically important class of stable NO adducts called S-nitrosothiols (SNO's). This stable pool of NO has been postulated to act as a source of bioactive NO and as such appears to be critically important in health and disease, given the centrality of NO in cellular homeostasis (Stamler et al., *Proc. Natl. Acad. Sci.* USA, 89:7674-7677 (1992)). Protein SNO's play broad roles in cardiovascular, respiratory, metabolic, gastrointestinal, immune and central nervous system function (Foster et al., 2003, *Trends in Molecular Medicine* Volume 9, Issue 4, April 2003, pages 160-168). One of the most studied SNO's in biological systems is S-nitrosoglutathione (GSNO) (Gaston et al., *Proc. Natl. Acad. Sci. USA* 90:10957-10961 (1993)), an emerging key regulator in NO signaling since it is an efficient trans-nitrosating agent and appears to maintain an equilibrium with other S-nitrosated proteins (Liu et al., *Nature,* 410:490-494 (2001)) within cells. Given this pivotal position in the NO-SNO continuum, GSNO provides a therapeutically promising target to consider when NO modulation is pharmacologically warranted.

In light of this understanding of GSNO as a key regulator of NO homeostasis and cellular SNO levels, studies have focused on examining endogenous production of GSNO and SNO proteins, which occurs downstream from the production of the NO radical by the nitric oxide synthetase (NOS) enzymes. More recently there has been an increasing understanding of enzymatic catabolism of GSNO which has an important role in governing available concentrations of GSNO and consequently available NO and SNO's.

Central to this understanding of GSNO catabolism, researchers have recently identified a highly conserved S-nitrosoglutathione reductase (GSNOR) (Jensen et al., *Biochem J.,* 331:659-668 (1998); Liu et al., 2001). GSNOR is also known as glutathione-dependent formaldehyde dehydrogenase (GS-FDH), alcohol dehydrogenase 3 (ADH-3) (Uotila and Koivusalo, *Coenzymes and Cofactors.,* D. Dolphin, ed. pp. 517-551 (New York, John Wiley & Sons, 1989)), and alcohol dehydrogenase 5 (ADH-5). Importantly GSNOR shows greater activity toward GSNO than other substrates (Jensen et al., 1998; Liu et al., 2001) and appears to mediate important protein and peptide denitrosating activity in bacteria, plants, and animals. GSNOR appears to be the major GSNO-metabolizing enzyme in eukaryotes (Liu et al., 2001). Thus, GSNO can accumulate in biological compartments where GSNOR activity is low or absent (e.g. airway lining fluid) (Gaston et al., 1993).

Yeast deficient in GSNOR accumulate S-nitrosylated proteins which are not substrates of the enzyme, which is strongly suggestive that GSNO exists in equilibrium with SNO-proteins (Liu et al., 2001). Precise enzymatic control over ambient levels of GSNO and thus SNO-proteins raises the possibility that GSNO/GSNOR may play roles across a host of physiological and pathological functions including protection against nitrosative stress wherein NO is produced in excess of physiologic needs. Indeed, GSNO specifically has been implicated in physiologic processes ranging from the drive to breathe (Lipton et al., *Nature,* 413:171-174 (2001)) to regulation of the cystic fibrosis transmembrane regulator (Zaman et al., *Biochem Biophys Res Commun,* 284: 65-70 (2001), to regulation of vascular tone, thrombosis and platelet function (de Belder et al., *Cardiovasc Res.* 1994 May; 28(5):691-4. (1994); Z. Kaposzta, A et al., *Circulation;* 106 (24): 3057-3062, 2002) as well as host defense (de Jesus-Berrios et al., *Curr. Biol.,* 13:1963-1968 (2003)). Other studies have found that GSNOR protects yeast cells against nitrosative stress both in vitro (Liu et al., 2001) and in vivo (de Jesus-Berrios et al., 2003).

Collectively data suggest GSNOR as a primary physiological ligand for the enzyme S-nitrosoglutathione reductase (GSNOR), which catabolizes GSNO and consequently reduces available SNO's and NO in biological systems (Liu et al., 2001), (Liu et al., *Cell,* (2004), 116(4), 617-628), and (Que et al., *Science,* 2005, 308, (5728):1618-1621). As such, this enzyme plays a central role in regulating local and systemic bioactive NO. Since perturbations in NO bioavailability has been linked to the pathogenesis of numerous disease states, including hypertension, atherosclerosis, thrombosis, asthma, gastrointestinal disorders, inflammation and cancer, agents that regulate GSNOR activity are candidate therapeutic agents for treating diseases associated with nitric oxide imbalance.

Currently, there is a great need in the art for diagnostics, prophylaxis, ameliorations, and treatments for medical conditions relating to a disease or condition characterized by overstimulation of NK3. There is also a need in the art for diagnostics, prophylaxis, ameliorations, and treatments for medical conditions relating to a disease or condition characterized by increased NO synthesis and/or increased NO bioactivity. In addition, there is a significant need for novel compounds, compositions and methods for preventing, ameliorating, or reversing other NK3 associated disorders and/or other NO-associated disorders. The present invention satisfies these needs.

SUMMARY

The present invention provides novel dihydropyrimidin-2 (1H)-one compounds useful as Neurokinin-3 ("NK3") receptor antagonists. The invention encompasses pharmaceutically acceptable salts, prodrugs, and metabolites of the described compounds. Also encompassed by the invention are pharmaceutical compositions comprising at least one compound of the invention and at least one pharmaceutically acceptable carrier. In some embodiments, the dihydropyrimidin-2(1H)-ones of the present invention are both NK3 receptor antagonists and S-nitrosoglutathione reductase (GSNOR) inhibitors (see provisional application U.S. 61/245,902 filed on Sep. 25, 2009 and PCT International Application Serial No. PCT/US10/50164 filed on Sep. 24, 2010, both incorporated herein by reference in their entirety, for additional discussion of GSNOR and GSNOR inhibitors).

The compositions of the present invention can be prepared in any suitable pharmaceutically acceptable dosage form.

The methods of the invention encompass administration with one or more secondary active agents. Such administration can be sequential or in a combination composition.

The present invention provides novel dihydropyrimidin-2 (1H)-one compounds useful as neurokinin-3 receptor antagonists. The tachykinins, substance P (SP), neurokinin A (NKA), and neurokinin B (NKB), are structurally similar members of a family of neuropeptides. Each of these is an agonist of the receptor types, neurokinin-1 receptor (NK1), neurokinin-2 receptor (NK2), and neurokinin-3 receptor (NK3), which are so defined according to their unique amino acid sequence and their relative abilities to bind tachykinins with high affinity and to be activated by the natural agonists, SP, NKA, and NKB, respectively (see also U.S. Pat. No. 5,434,158, which is herein incorporated by reference). In some embodiments, the dihydropyrimidin-2(1H)-ones of the present invention are NK3 receptor antagonists.

The present invention provides a method for antagonizing the neurokinin-3 (NK3) receptor. Such a method comprises administering a therapeutically effective amount of a pharmaceutical composition comprising at least one NK3 receptor antagonist or a pharmaceutically acceptable salt thereof, a prodrug or metabolite thereof, in combination with at least one pharmaceutically acceptable carrier. The NK3 receptor antagonist can be a novel compound according to the invention, or it can be a known compound which previously was not known to be an NK3 receptor antagonist.

Although methods and materials similar or equivalent to those described herein can be used in the practice or testing of the present invention, suitable methods and materials are described below. All publicly available publications, patent applications, patents, and other references mentioned herein are incorporated by reference in their entirety. In the case of conflict, the present specification, including definitions, will control.

Both the foregoing summary and the following detailed description are exemplary and explanatory and are intended to provide further details of the compositions and methods as claimed. Other objects, advantages, and novel features will be readily apparent to those skilled in the art from the following detailed description.

DETAILED DESCRIPTION

A. Overview of the Invention

The present invention provides pharmaceutical agents that are potent antagonists of the NK3 receptor. In particular, provided are substituted dihydropyrimidin-2(1H)-one analogs having the structures depicted below (Formula I), or a pharmaceutically acceptable salt, stereoisomer, or prodrug thereof.

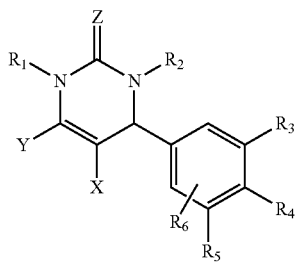

I wherein
X is selected from the group consisting of aryl, substituted aryl, heteroaryl, substituted heteroaryl, cycloalkyl, substituted cycloalkyl, heterocyclyl, and substituted heterocyclyl, each having 6 members or less in the ring;
Y is selected from the group consisting of aryl, substituted aryl, heteroaryl, substituted heteroaryl, cycloalkyl, substituted cycloalkyl, heterocyclyl, and substituted heterocyclyl;
Z is selected from the group consisting of O, S and NR$_7$;
R$_1$, R$_2$ and R$_7$ are independently selected from the group consisting of hydrogen, and C$_1$-C$_6$ alkyl;
R$_3$ is selected from the group consisting of hydrogen, nitro, cyano, carboxy, carbamoyl, methylsulfonamido, fluoro, chloro, bromo, hydroxy, methylsulfonyl, and methylsulfinyl, isoxazol-4-yl, C$_1$-C$_6$ alkoxy, —C(NH)NHOH, sulfonic acid, and acetyl;
R$_4$ is selected from the group consisting of hydrogen, hydroxy, methoxy, carboxy, and tetrazol-5-yl;
or optionally R$_3$ and R$_4$, taken together can form a heterocycle;
R$_5$ is selected from the group consisting of hydrogen, hydroxy, carboxy, chloro, fluoro, cyano, —O(CH$_2$)$_{1-6}$NMe$_2$, C$_1$-C$_6$ alkyl, —O(CH$_2$)$_{1-6}$OCH$_3$, —O(CH$_2$)$_{1-6}$OH, acetyl, CF$_3$, and C$_1$-C$_6$ alkoxy;
or optionally R$_4$ and R$_5$, taken together can form a heterocycle; and
R$_6$ is selected from the group consisting of hydrogen and hydroxy.

As used in this context, the term "analog" refers to a compound having similar chemical structure and function as compounds of Formula I that retains the dihydropyrimidin-2(1H)-one ring.

Some dihydropyrimidin-2(1H)-one analogs of the invention can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of a compound including tautomeric forms of the compound.

Illustrative compounds having asymmetric centers can exist in different enantiomeric and diastereomeric forms. A compound can exist in the form of an optical isomer or a diastereomer. Accordingly, the invention encompasses compounds in the forms of their optical isomers, diastereomers and mixtures thereof, including racemic mixtures.

It should be noted that if there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereoisomers of the described compound.

B. NK3 Receptor Antagonists

1. Inventive Compounds

In one of its aspects the present invention provides pharmaceutical agents that are potent antagonists of the NK3 receptor. In particular, provided are substituted dihydropyrimidin-2(1H)-one analogs having the structures depicted below (Formula I), or a pharmaceutically acceptable salt, stereoisomer, or prodrug thereof:

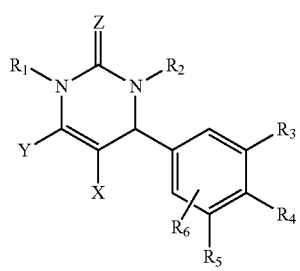

I wherein
X is selected from the group consisting of aryl, substituted aryl, heteroaryl, substituted heteroaryl, cycloalkyl, substituted cycloalkyl, heterocyclyl, and substituted heterocyclyl, each having 6 members or less in the ring;

Y is selected from the group consisting of aryl, substituted aryl, heteroaryl, substituted heteroaryl, cycloalkyl, substituted cycloalkyl, heterocyclyl, and substituted heterocyclyl;

Z is selected from the group consisting of O, S and $NR_7$;

$R_1$, $R_2$ and $R_7$ are independently selected from the group consisting of hydrogen, and $C_1$-$C_6$ alkyl;

$R_3$ is selected from the group consisting of hydrogen, nitro, cyano, carboxyl, carbamoyl, methylsulfonamido, fluoro, chloro, bromo, hydroxy, methylsulfonyl, and methylsulfinyl, isoxazol-4-yl, $C_1$-$C_6$ alkoxy, —C(NH)NHOH, sulfonic acid, and acetyl;

$R_4$ is selected from the group consisting of hydrogen, hydroxy, methoxy, carboxyl, and tetrazol-5-yl;

or optionally $R_3$ and $R_4$, taken together can form a heterocycle;

$R_5$ is selected from the group consisting of hydrogen, hydroxyl, carboxy, chloro, fluoro, cyano, —$O(CH_2)_{1-6}NMe_2$, $C_1$-$C_6$ alkyl, —$O(CH_2)_{1-6}OCH_3$, —$O(CH_2)_{1-6}OH$, acetyl, $CF_3$, and $C_1$-$C_6$ alkoxy;

or optionally $R_4$ and $R_5$, taken together can form a heterocycle; and $R_6$ is selected from the group consisting of hydrogen and hydroxyl.

In a further aspect of the invention, $R_1$, $R_2$ and $R_7$ are independently selected from the group consisting of hydrogen and methyl; $R_3$ is selected from the group consisting of hydrogen, nitro, cyano, carboxy, carbamoyl, methylsulfonamido, fluoro, chloro, bromo, methylsulfonyl, and methylsulfinyl, isoxazol-4-yl, $C_1$-$C_6$ alkoxy, —C(NH)NHOH, sulfonic acid, and acetyl; $R_4$ is selected from the group consisting of hydroxy, carboxy, and tetrazol-5-yl; $R_5$ is selected from the group consisting of hydrogen, hydroxyl, carboxy, chloro, fluoro, cyano, —$O(CH_2)_2NMe_2$, $C_1$-$C_6$ alkyl, —$O(CH_2)_2OCH_3$, —$O(CH_2)_2OH$, acetyl, $CF_3$, methoxy, ethoxy, isopropoxy, and n-propoxy; and $R_6$ is hydrogen.

In a further aspect of the invention, $R_1$, $R_2$ and $R_7$ are independently selected from the group consisting of hydrogen and methyl; $R_3$ is selected from the group consisting of nitro, cyano, carboxy, carbamoyl, methylsulfonamido, fluoro, chloro, bromo, hydroxy, methylsulfonyl, and methylsulfinyl, isoxazol-4-yl, $C_1$-$C_6$ alkoxy, —C(NH)NHOH, sulfonic acid, and acetyl; $R_4$ is selected from the group consisting of hydroxy, carboxy, and tetrazol-5-yl; $R_5$ is selected from the group consisting of hydrogen, hydroxy, carboxy, chloro, fluoro, cyano, —$O(CH_2)_2NMe_2$, $C_1$-$C_6$ alkyl, —$O(CH_2)_2OCH_3$, —$O(CH_2)_2OH$, acetyl, $CF_3$, methoxy, ethoxy, isopropoxy, and n-propoxy; and $R_6$ is hydrogen.

In a further aspect of the invention, suitable identities for X include, but are not limited to phenyl, substituted phenyl, thiophen-yl, substituted thiophen-yl, thiazol-yl, substituted thiazol-yl, pyrazin-yl, substituted pyrazin-yl, pyridin-yl, and substituted pyridin-yl, cyclohexyl, and substituted cyclohexyl.

In a further aspect of the invention, suitable identities for X include, but are not limited to, phenyl, thiophen-2-yl, thiophen-3-yl, thiazol-2-yl, 2-fluorophenyl, p-tolyl, m-tolyl, biphenyl-4-yl, 4-methoxyphenyl, 3-chlorophenyl, 3,4-dichlorophenyl, 3-methoxyphenyl, 3,4-dimethoxyphenyl, 4-bromophenyl, o-tolyl, 4-chlorophenyl, 2-chlorophenyl, 3-cyanophenyl, 3,4-difluorophenyl, 4-cyanophenyl, 3-carbamoylphenyl, pyrazin-2-yl, biphenyl-3-yl, 2-cyanophenyl, pyridin-4-yl, and pyridin-3-yl, 4-(dimethylamino)phenyl, 3-fluorophenyl, 3-ethylphenyl, and cyclohexyl.

In a further aspect of the invention, suitable identities for Y include, but are not limited to, phenyl, substituted phenyl, thiophen-yl, substituted thiophen-yl, thiazol-yl, substituted thiazol-yl, pyrazin-yl, substituted pyrazin-yl, pyridin-yl, substituted pyridin-yl, furan-yl, substituted furan-yl, benzo[d][1,3]dioxol-yl, substituted benzo[d][1,3]dioxol-yl, imidazol-yl, substituted imidazol-yl, naphthalen-yl, substituted naphthalen-yl, pyrrol-yl, substituted pyrrol-yl, pyrazol-yl, substituted pyrazol-yl, tetrahydrofuran-yl, substituted tetrahydrofuran-yl, cyclopentyl, substituted cyclopentyl, cyclohexyl, and substituted cyclohexyl.

In a further aspect of the invention, suitable identities for Y include, but are not limited to, phenyl, 3-methoxyphenyl, p-tolyl, 4-methoxyphenyl, 3,5-dichlorophenyl, 3-fluorophenyl, 4-bromophenyl, biphenyl-4-yl, 4-fluorophenyl, 4-chlorophenyl, 3-chlorophenyl, 3,4-dimethoxyphenyl, 3-fluoro-4-methoxyphenyl, 4-chloro-3-fluorophenyl, 3-chloro-4-fluorophenyl, 3,4-difluorophenyl, 3,5-difluorophenyl, 3,4-dichlorophenyl, 4-hydroxyphenyl, 2,4-difluorophenyl, furan-3-yl, 2-chlorophenyl, 3-cyanophenyl, 4-(dimethylamino)phenyl, 2-fluorophenyl, 4-morpholinophenyl, 4-aminophenyl, naphthal-2-yl, benzo[d][1,3]dioxol-5-yl, 4-cyanophenyl, naphthal-3-yl, naphthal-4-yl, 4-acetamidophenyl, thiophen-2-yl, thiophen-3-yl, 1-methyl-1H-imidazol-4-yl, naphthalene-1-yl, methyl phenylcarbamate, and naphthalene-2-yl, 4-(methanesulfonamido)phenyl, 1H-pyrrol-3-yl, 1-(phenylsulfonyl)-1H-pyrrol-3-yl, furan-2-yl, 4-(trifluoromethyl)phenyl, o-tolyl, 1-methyl-1H-pyrazol-4-yl, 1-methyl-1H-pyrazol-3-yl, 3-chloro-5-fluorophenyl, 3-hydroxyphenyl, pyrazin-2-yl, quinolin-6-yl, isoquinolin-6-yl, 1-methyl-1H-pyrazol-5-yl, tetrahydrofuran-2-yl, cyclopentyl, tetrahydrofuran-3-yl, and cyclohexyl.

In a further aspect of the invention, suitable compounds of formula I include, but are not limited to:

4-(3-ethoxy-4-hydroxy-5-nitrophenyl)-5,6-diphenyl-3,4-dihydropyrimidin-2(1H)-one;

(R)-4-(3-ethoxy-4-hydroxy-5-nitrophenyl)-5,6-diphenyl-3,4-dihydropyrimidin-2(1H)-one;

4-(3-ethoxy-4-hydroxy-5-nitrophenyl)-6-phenyl-5-(thiophen-2-yl)-3,4-dihydropyrimidin-2(1H)-one;

4-(3-ethoxy-4-hydroxy-5-nitrophenyl)-6-phenyl-5-(thiophen-3-yl)-3,4-dihydropyrimidin-2(1H)-one;

(R)-4-(3-ethoxy-4-hydroxy-5-nitrophenyl)-6-phenyl-5-(thiophen-3-yl)-3,4-dihydropyrimidin-2(1H)-one;

4-(3-ethoxy-4-hydroxy-5-nitrophenyl)-5,6-diphenyl-3,4-dihydropyrimidine-2(1H)-thione;

4-(4-hydroxy-3-methoxy-5-nitrophenyl)-5,6-diphenyl-3,4-dihydropyrimidin-2(1H)-one;

4-(3,4-dihydroxy-5-nitrophenyl)-5,6-diphenyl-3,4-dihydropyrimidin-2(1H)-one;

4-(3-ethoxy-4-hydroxy-5-nitrophenyl)-1-methyl-5,6-diphenyl-3,4-dihydropyrimidin-2(1H)-one;

4-(3-ethoxy-4-hydroxy-5-nitrophenyl)-6-phenyl-5-(thiazol-2-yl)-3,4-dihydropyrimidin-2(1H)-one;

4-(3-ethoxy-4-hydroxy-5-nitrophenyl)-5-(2-fluorophenyl)-6-phenyl-3,4-dihydropyrimidin-2(1H)-one;

4-(3-ethoxy-4-hydroxy-5-nitrophenyl)-6-phenyl-5-p-tolyl-3,4-dihydropyrimidin-2(1H)-one;

4-(3-ethoxy-4-hydroxy-5-nitrophenyl)-6-(3-methoxyphenyl)-5-phenyl-3,4-dihydropyrimidin-2(1H)-one;

4-(3-ethoxy-4-hydroxy-5-nitrophenyl)-5-phenyl-6-p-tolyl-3,4-dihydropyrimidin-2(1H)-one;

4-(3-ethoxy-4-hydroxy-5-nitrophenyl)-6-phenyl-5-m-tolyl-3,4-dihydropyrimidin-2(1H)-one;

5-(biphenyl-4-yl)-4-(3-ethoxy-4-hydroxy-5-nitrophenyl)-6-phenyl-3,4-dihydropyrimidin-2(1H)-one;

4-(3-ethoxy-4-hydroxy-5-nitrophenyl)-5-(4-methoxyphenyl)-6-phenyl-3,4-dihydropyrimidin-2(1H)-one;

4-(3-ethoxy-4-hydroxy-5-nitrophenyl)-6-(4-methoxyphenyl)-5-phenyl-3,4-dihydropyrimidin-2(1H)-one;

5-(3-chlorophenyl)-4-(3-ethoxy-4-hydroxy-5-nitrophenyl)-6-phenyl-3,4-dihydropyrimidin-2(1H)-one;
5-(3,4-dichlorophenyl)-4-(3-ethoxy-4-hydroxy-5-nitrophenyl)-6-phenyl-3,4-dihydropyrimidin-2(1H)-one;
4-(3-ethoxy-4-hydroxy-5-nitrophenyl)-5-(3-methoxyphenyl)-6-phenyl-3,4-dihydropyrimidin-2(1H)-one;
5-(3,4-dimethoxyphenyl)-4-(3-ethoxy-4-hydroxy-5-nitrophenyl)-6-phenyl-3,4-dihydropyrimidin-2(1H)-one;
5-(4-bromophenyl)-4-(3-ethoxy-4-hydroxy-5-nitrophenyl)-6-phenyl-3,4-dihydropyrimidin-2(1H)-one;
4-(3-ethoxy-4-hydroxy-5-nitrophenyl)-6-phenyl-5-o-tolyl-3,4-dihydropyrimidin-2(1H)-one;
5-(4-chlorophenyl)-4-(3-ethoxy-4-hydroxy-5-nitrophenyl)-6-phenyl-3,4-dihydropyrimidin-2(1H)-one;
5-(2-chlorophenyl)-4-(3-ethoxy-4-hydroxy-5-nitrophenyl)-6-phenyl-3,4-dihydropyrimidin-2(1H)-one;
3-(4-(3-ethoxy-4-hydroxy-5-nitrophenyl)-2-oxo-6-phenyl-1,2,3,4-tetrahydropyrimidin-5-yl)benzonitrile;
5-(3,4-difluorophenyl)-4-(3-ethoxy-4-hydroxy-5-nitrophenyl)-6-phenyl-3,4-dihydropyrimidin-2(1H)-one;
6-(3,5-dichlorophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(3-fluorophenyl)-5-phenyl-3,4-dihydropyrimidin-2(1H)-one;
6-(4-bromophenyl)-4-(3-ethoxy-4-hydroxy-5-nitrophenyl)-5-phenyl-3,4-dihydropyrimidin-2(1H)-one;
6-(biphenyl-4-yl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(4-fluorophenyl)-5-phenyl-3,4-dihydropyrimidin-2(1H)-one;
6-(4-chlorophenyl)-4-(3-ethoxy-4-hydroxy-5-nitrophenyl)-5-phenyl-3,4-dihydropyrimidin-2(1H)-one;
6-(3-chlorophenyl)-4-(3-ethoxy-4-hydroxy-5-nitrophenyl)-5-phenyl-3,4-dihydropyrimidin-2(1H)-one;
6-(3,4-dimethoxyphenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(3-fluoro-4-methoxyphenyl)-5-phenyl-3,4-dihydropyrimidin-2(1H)-one;
4-(3-fluoro-5-hydroxy-4-methoxyphenyl)-5,6-diphenyl-3,4-dihydropyrimidin-2(1H)-one;
4-(3-ethoxy-4-hydroxy-5-nitrophenyl)-1,3-dimethyl-5,6-diphenyl-3,4-dihydropyrimidin-2(1H)-one;
4-(4-(3-ethoxy-4-hydroxy-5-nitrophenyl)-2-oxo-6-phenyl-1,2,3,4-tetrahydropyrimidin-5-yl)benzonitrile;
6-(4-chloro-3-fluorophenyl)-4-(3-ethoxy-4-hydroxy-5-nitrophenyl)-5-phenyl-3,4-dihydropyrimidin-2(1H)-one;
6-(3-chloro-4-fluorophenyl)-4-(3-ethoxy-4-hydroxy-5-nitrophenyl)-5-phenyl-3,4-dihydropyrimidin-2(1H)-one;
6-(3,4-difluorophenyl)-4-(3-ethoxy-4-hydroxy-5-nitrophenyl)-5-phenyl-3,4-dihydropyrimidin-2(1H)-one;
6-(3,5-difluorophenyl)-4-(3-ethoxy-4-hydroxy-5-nitrophenyl)-5-phenyl-3,4-dihydropyrimidin-2(1H)-one;
6-(3,4-dichlorophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(4-hydroxyphenyl)-5-phenyl-3,4-dihydropyrimidin-2(1H)-one;
6-(2,4-difluorophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(furan-3-yl)-5-phenyl-3,4-dihydropyrimidin-2(1H)-one;
6-(2-chlorophenyl)-4-(3-ethoxy-4-hydroxy-5-nitrophenyl)-5-phenyl-3,4-dihydropyrimidin-2(1H)-one;
3-(4-(3-ethoxy-4-hydroxy-5-nitrophenyl)-2-oxo-6-phenyl-1,2,3,4-tetrahydropyrimidin-5-yl)benzamide;
3-(6-(3-ethoxy-4-hydroxy-5-nitrophenyl)-2-oxo-5-phenyl-1,2,3,6-tetrahydropyrimidin-4-yl)benzonitrile;
6-(4-(dimethylamino)phenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(2-fluorophenyl)-5-phenyl-3,4-dihydropyrimidin-2(1H)-one;
4-(3-ethoxy-4-hydroxy-5-nitrophenyl)-6-(4-morpholinophenyl)-5-phenyl-3,4-dihydropyrimidin-2(1H)-one;
6-(4-aminophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-phenyl-5-(pyrazin-2-yl)-3,4-dihydropyrimidin-2(1H)-one;
4-(3-ethoxy-4-hydroxy-5-nitrophenyl)-5-phenyl-6-(pyridin-2-yl)-3,4-dihydropyrimidin-2(1H)-one;
5-(biphenyl-3-yl)-4-(3-ethoxy-4-hydroxy-5-nitrophenyl)-6-phenyl-3,4-dihydropyrimidin-2(1H)-one;
6-(benzo[d][1,3]dioxol-5-yl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-3-methyl-5,6-diphenyl-3,4-dihydropyrimidin-2(1H)-one;
4-(6-(3-ethoxy-4-hydroxy-5-nitrophenyl)-2-oxo-5-phenyl-1,2,3,6-tetrahydropyrimidin-4-yl)benzonitrile;
4-(3-ethoxy-5-fluoro-4-hydroxyphenyl)-5,6-diphenyl-3,4-dihydropyrimidin-2(1H)-one;
4-(3-ethoxy-4-hydroxy-5-nitrophenyl)-5-phenyl-6-(pyridin-3-yl)-3,4-dihydropyrimidin-2(1H)-one;
(R)-4-(3-ethoxy-4-hydroxy-5-nitrophenyl)-5-phenyl-6-(pyridin-3-yl)-3,4-dihydropyrimidin-2(1H)-one;
4-(3-fluoro-4-hydroxy-5-methoxyphenyl)-5,6-diphenyl-3,4-dihydropyrimidin-2(1H)-one;
3-ethoxy-2-hydroxy-5-(2-oxo-5,6-diphenyl-1,2,3,4-tetrahydropyrimidin-4-yl)benzonitrile;
2-(4-(3-ethoxy-4-hydroxy-5-nitrophenyl)-2-oxo-6-phenyl-1,2,3,4-tetrahydropyrimidin-5-yl)benzonitrile;
4-(3-ethoxy-4-hydroxy-5-nitrophenyl)-5-phenyl-6-(pyridin-4-yl)-3,4-dihydropyrimidin-2(1H)-one;
7-ethoxy-5-(2-oxo-5,6-diphenyl-1,2,3,4-tetrahydropyrimidin-4-yl)benzo[d]oxazol-2(3H)-one;
N-(4-(6-(3-ethoxy-4-hydroxy-5-nitrophenyl)-2-oxo-5-phenyl-1,2,3,6-tetrahydropyrimidin-4-yl)phenyl)acetamide;
4-(3-ethoxy-4-hydroxy-5-nitrophenyl)-6-phenyl-5-(pyridin-4-yl)-3,4-dihydropyrimidin-2(1H)-one;
N-(3-ethoxy-2-hydroxy-5-(2-oxo-5,6-diphenyl-1,2,3,4-tetrahydropyrimidin-4-yl)phenyl)methanesulfonamide;
N-(2-hydroxy-3-methoxy-5-(2-oxo-5,6-diphenyl-1,2,3,4-tetrahydropyrimidin-4-yl)phenyl)methanesulfonamide;
3-ethoxy-2-hydroxy-5-(2-oxo-5,6-diphenyl-1,2,3,4-tetrahydropyrimidin-4-yl)benzoic acid;
4-(3-ethoxy-4-hydroxy-5-nitrophenyl)-5-phenyl-6-(thiophen-2-yl)-3,4-dihydropyrimidin-2(1H)-one;
4-(3-ethoxy-4-hydroxy-5-nitrophenyl)-5-phenyl-6-(thiophen-3-yl)-3,4-dihydropyrimidin-2(1H)-one;
4-(3-ethoxy-4-hydroxy-5-nitrophenyl)-6-(1-methyl-1H-imidazol-4-yl)-5-phenyl-3,4-dihydropyrimidin-2(1H)-one;
4-(3-ethoxy-4-hydroxy-5-nitrophenyl)-6-(naphthalen-1-yl)-5-phenyl-3,4-dihydropyrimidin-2(1H)-one;
3-ethoxy-2-hydroxy-5-(2-oxo-5,6-diphenyl-1,2,3,4-tetrahydropyrimidin-4-yl)benzamide;
methyl 4-(6-(3-ethoxy-4-hydroxy-5-nitrophenyl)-2-oxo-5-phenyl-1,2,3,6-tetrahydropyrimidin-4-yl)phenylcarbamate;
4-(3-ethoxy-4-hydroxy-5-nitrophenyl)-6-phenyl-5-(pyridin-3-yl)-3,4-dihydropyrimidin-2(1H)-one;
4-(3-ethoxy-4-hydroxy-5-nitrophenyl)-6-(naphthalen-2-yl)-5-phenyl-3,4-dihydropyrimidin-2(1H)-one;
2-hydroxy-5-(2-oxo-5,6-diphenyl-1,2,3,4-tetrahydropyrimidin-4-yl)benzoic acid;
4-(4-hydroxy-3-methoxyphenyl)-5,6-diphenyl-3,4-dihydropyrimidin-2(1H)-one;

5-(4-(dimethylamino)phenyl)-4-(3-ethoxy-4-hydroxy-5-nitrophenyl)-6-phenyl-3,4-dihydropyrimidin-2(1H)-one;
4-(8-nitro-2,3-dihydrobenzo[b][1,4]dioxin-6-yl)-5,6-diphenyl-3,4-dihydropyrimidin-2(1H)-one;
4-(2-oxo-5,6-diphenyl-1,2,3,4-tetrahydropyrimidin-4-yl) benzoic acid;
4-(3-(isoxazol-4-yl)phenyl)-5,6-diphenyl-3,4-dihydropyrimidin-2(1H)-one;
1,1'-(2-hydroxy-5-(2-oxo-5,6-diphenyl-1,2,3,4-tetrahydropyrimidin-4-yl)-1,3-phenylene)diethanone;
3-(2-oxo-5,6-diphenyl-1,2,3,4-tetrahydropyrimidin-4-yl) benzoic acid;
2-hydroxy-3-(2-oxo-5,6-diphenyl-1,2,3,4-tetrahydropyrimidin-4-yl)benzonitrile;
4-(4-hydroxy-3-nitrophenyl)-5,6-diphenyl-3,4-dihydropyrimidin-2(1H)-one;
2-hydroxy-5-(2-oxo-5,6-diphenyl-1,2,3,4-tetrahydropyrimidin-4-yl)benzonitrile;
2-ethoxy-4-(2-oxo-5,6-diphenyl-1,2,3,4-tetrahydropyrimidin-4-yl)benzoic acid;
3-(2-oxo-5,6-diphenyl-1,2,3,4-tetrahydropyrimidin-4-yl) benzamide;
N-hydroxy-3-(2-oxo-5,6-diphenyl-1,2,3,4-tetrahydropyrimidin-4-yl)benzimidamide;
4-(3-bromo-5-ethoxy-4-hydroxyphenyl)-5,6-diphenyl-3,4-dihydropyrimidin-2(1H)-one;
N-(4-(6-(3-ethoxy-4-hydroxy-5-nitrophenyl)-2-oxo-5-phenyl-1,2,3,6-tetrahydropyrimidin-4-yl)phenyl)methanesulfonamide;
4-(4-hydroxy-3-isopropoxy-5-nitrophenyl)-5,6-diphenyl-3,4-dihydropyrimidin-2(1H)-one;
4-(3-ethoxy-4-hydroxy-5-(methylsulfonyl)phenyl)-5,6-diphenyl-3,4-dihydropyrimidin-2(1H)-one;
4-(3-ethoxy-4-hydroxy-5-(methylsulfinyl)phenyl)-5,6-diphenyl-3,4-dihydropyrimidin-2(1H)-one;
3-ethoxy-2-hydroxy-5-(2-oxo-6-phenyl-5-(thiophen-3-yl)-1,2,3,4-tetrahydropyrimidin-4-yl)benzonitrile;
4-(3-ethoxy-4-hydroxy-5-nitrophenyl)-5-phenyl-6-(1H-pyrrol-3-yl)-3,4-dihydropyrimidin-2(1H)-one;
4-(3-ethoxy-4-hydroxy-5-nitrophenyl)-5-phenyl-6-(1-(phenylsulfonyl)-1H-pyrrol-3-yl)-3,4-dihydropyrimidin-2(1H)-one;
4-(3-ethoxy-4-hydroxy-5-nitrophenyl)-6-(4-fluorophenyl)-5-(3-methoxyphenyl)-3,4-dihydropyrimidin-2(1H)-one;
4-(3-ethoxy-4-hydroxy-5-nitrophenyl)-6-(4-fluorophenyl)-5-(thiophen-3-yl)-3,4-dihydropyrimidin-2(1H)-one;
2-hydroxy-3-nitro-5-(2-oxo-5,6-diphenyl-1,2,3,4-tetrahydropyrimidin-4-yl)benzoic acid;
4-(3-ethoxy-4-hydroxy-5-nitrophenyl)-6-(furan-2-yl)-5-phenyl-3,4-dihydropyrimidin-2(1H)-one;
2-ethoxy-4-(2-imino-5,6-diphenyl-1,2,3,4-tetrahydropyrimidin-4-yl)-6-nitrophenol;
4-(3-ethoxy-4-hydroxy-5-nitrophenyl)-5-phenyl-6-(4-(trifluoromethyl)phenyl)-3,4-dihydropyrimidin-2(1H)-one;
4-(3-ethoxy-4-hydroxy-5-nitrophenyl)-5-phenyl-6-o-tolyl-3,4-dihydropyrimidin-2(1H)-one;
4-(3-ethoxy-4-hydroxy-5-nitrophenyl)-5-(3-fluorophenyl)-6-phenyl-3,4-dihydropyrimidin-2(1H)-one;
4-(3-ethoxy-4-hydroxy-5-nitrophenyl)-6-(pyridin-3-yl)-5-(thiophen-3-yl)-3,4-dihydropyrimidin-2(1H)-one;
(Z)-2-ethoxy-4-(2-(methylimino)-5,6-diphenyl-1,2,3,4-tetrahydropyrimidin-4-yl)-6-nitrophenol;
4-(3-ethoxy-4-hydroxy-5-nitrophenyl)-6-(1-methyl-1H-pyrazol-4-yl)-5-(thiophen-3-yl)-3,4-dihydropyrimidin-2(1H)-one;
4-(3-ethoxy-4-hydroxy-5-nitrophenyl)-6-(1-methyl-1H-pyrazol-3-yl)-5-(thiophen-3-yl)-3,4-dihydropyrimidin-2(1H)-one;
4-(3-chloro-4-hydroxy-5-nitrophenyl)-5,6-diphenyl-3,4-dihydropyrimidin-2(1H)-one;
6-(3-chloro-5-fluorophenyl)-4-(3-ethoxy-4-hydroxy-5-nitrophenyl)-5-phenyl-3,4-dihydropyrimidin-2(1H)-one;
2-hydroxy-3-nitro-5-(2-oxo-5,6-diphenyl-1,2,3,4-tetrahydropyrimidin-4-yl)benzonitrile;
2-hydroxy-5-(2-oxo-5,6-diphenyl-1,2,3,4-tetrahydropyrimidin-4-yl)benzenesulfonic acid;
(R)-3-ethoxy-2-hydroxy-5-(2-oxo-6-(pyridin-3-yl)-5-(thiophen-3-yl)-1,2,3,4-tetrahydropyrimidin-4-yl)benzoic acid;
3-ethoxy-2-hydroxy-5-(2-oxo-6-(pyridin-3-yl)-5-(thiophen-3-yl)-1,2,3,4-tetrahydropyrimidin-4-yl)benzoic acid;
4-(3-fluoro-4-hydroxy-5-nitrophenyl)-5,6-diphenyl-3,4-dihydropyrimidin-2(1H)-one;
3-ethoxy-2-hydroxy-5-(2-oxo-6-(pyridin-3-yl)-5-(thiophen-3-yl)-1,2,3,4-tetrahydropyrimidin-4-yl)benzonitrile;
4-(3-ethoxy-4-hydroxy-5-nitrophenyl)-6-(3-hydroxyphenyl)-5-phenyl-3,4-dihydropyrimidin-2(1H)-one;
4-(4-hydroxy-3-nitro-5-propoxyphenyl)-5,6-diphenyl-3,4-dihydropyrimidin-2(1H)-one;
4-(3-ethoxy-4-hydroxy-5-nitrophenyl)-6-(pyrazin-2-yl)-5-(thiophen-3-yl)-3,4-dihydropyrimidin-2(1H)-one;
4-(3-ethoxy-4-hydroxy-5-nitrophenyl)-5-phenyl-6-(quinolin-6-yl)-3,4-dihydropyrimidin-2(1H)-one;
4-(3-ethoxy-4-hydroxy-5-nitrophenyl)-6-(isoquinolin-6-yl)-5-phenyl-3,4-dihydropyrimidin-2(1H)-one;
4-(3-ethoxy-4-hydroxy-5-nitrophenyl)-5-(3-methoxyphenyl)-6-(pyridin-3-yl)-3,4-dihydropyrimidin-2(1H)-one;
3-ethoxy-2-hydroxy-5-(5-(3-methoxyphenyl)-2-oxo-6-(pyridin-3-yl)-1,2,3,4-tetrahydropyrimidin-4-yl)benzoic acid;
4-(3-ethoxy-4-hydroxy-5-nitrophenyl)-6-(pyridin-4-yl)-5-(thiophen-3-yl)-3,4-dihydropyrimidin-2(1H)-one;
4-(4-hydroxy-3-(2-hydroxyethoxy)-5-nitrophenyl)-5,6-diphenyl-3,4-dihydropyrimidin-2(1H)-one;
2-hydroxy-4-(2-oxo-5,6-diphenyl-1,2,3,4-tetrahydropyrimidin-4-yl)benzoic acid;
4-(3-ethoxy-4-hydroxy-5-nitrophenyl)-6-(1-methyl-1H-pyrazol-5-yl)-5-(thiophen-3-yl)-3,4-dihydropyrimidin-2(1H)-one;
2-nitro-4-(2-oxo-5,6-diphenyl-1,2,3,4-tetrahydropyrimidin-4-yl)benzoic acid;
4-(3-ethoxy-4-hydroxy-5-nitrophenyl)-5-(3-ethylphenyl)-6-phenyl-3,4-dihydropyrimidin-2(1H)-one;
3-ethoxy-2-hydroxy-5-(6-(1-methyl-1H-pyrazol-4-yl)-2-oxo-5-(thiophen-3-yl)-1,2,3,4-tetrahydropyrimidin-4-yl) benzoic acid;
(R)-4-(3-ethoxy-4-hydroxy-5-nitrophenyl)-6-(pyridin-3-yl)-5-(thiophen-3-yl)-3,4-dihydropyrimidin-2(1H)-one;
2-chloro-4-(2-oxo-5,6-diphenyl-1,2,3,4-tetrahydropyrimidin-4-yl)benzoic acid;
(R)-3-ethoxy-2-hydroxy-5-(6-(1-methyl-1H-pyrazol-4-yl)-2-oxo-5-(thiophen-3-yl)-1,2,3,4-tetrahydropyrimidin-4-yl)benzoic acid;
(R)-4-(3-ethoxy-4-hydroxy-5-nitrophenyl)-6-(1-methyl-1H-pyrazol-3-yl)-5-(thiophen-3-yl)-3,4-dihydropyrimidin-2(1H)-one;
4-ethoxy-6-(2-oxo-5,6-diphenyl-1,2,3,4-tetrahydropyrimidin-4-yl)benzo[d]oxazol-2(3H)-one;
3-fluoro-2-hydroxy-5-(2-oxo-5,6-diphenyl-1,2,3,4-tetrahydropyrimidin-4-yl)benzoic acid;
2-fluoro-4-(2-oxo-5,6-diphenyl-1,2,3,4-tetrahydropyrimidin-4-yl)benzoic acid;

2-ethoxy-6-nitro-4-(2-oxo-5,6-diphenyl-1,2,3,4-tetrahydropyrimidin-4-yl)benzoic acid;
4-(4-hydroxy-3-nitro-5-(trifluoromethyl)phenyl)-5,6-diphenyl-3,4-dihydropyrimidin-2(1H)-one;
4-(4-hydroxy-3-(2-methoxyethoxy)-5-nitrophenyl)-5,6-diphenyl-3,4-dihydropyrimidin-2(1H)-one;
4-(4-hydroxy-3-nitro-5-propylphenyl)-5,6-diphenyl-3,4-dihydropyrimidin-2(1H)-one;
4-(2-oxo-5,6-diphenyl-1,2,3,4-tetrahydropyrimidin-4-yl)-2-(trifluoromethyl)benzoic acid;
2-fluoro-6-hydroxy-4-(2-oxo-5,6-diphenyl-1,2,3,4-tetrahydropyrimidin-4-yl)benzoic acid;
2-hydroxy-4-(6-(1-methyl-1H-pyrazol-4-yl)-2-oxo-5-(thiophen-3-yl)-1,2,3,4-tetrahydropyrimidin-4-yl)benzoic acid;
2-hydroxy-4-(2-oxo-5-phenyl-6-(pyridin-3-yl)-1,2,3,4-tetrahydropyrimidin-4-yl)benzoic acid;
2-ethoxy-6-hydroxy-4-(2-oxo-5,6-diphenyl-1,2,3,4-tetrahydropyrimidin-4-yl)benzoic acid;
4-(4-(2H-tetrazol-5-yl)phenyl)-5-phenyl-6-(pyridin-3-yl)-3,4-dihydropyrimidin-2(1H)-one;
2-chloro-6-hydroxy-4-(2-oxo-5,6-diphenyl-1,2,3,4-tetrahydropyrimidin-4-yl)benzoic acid;
4-(4-(2H-tetrazol-5-yl)phenyl)-5,6-diphenyl-3,4-dihydropyrimidin-2(1H)-one;
2-hydroxy-6-methoxy-4-(2-oxo-5,6-diphenyl-1,2,3,4-tetrahydropyrimidin-4-yl)benzoic acid;
4-(4-(2H-tetrazol-5-yl)phenyl)-6-(pyridin-3-yl)-5-(thiophen-3-yl)-3,4-dihydropyrimidin-2(1H)-one;
2-hydroxy-4-(6-(1-methyl-1H-pyrazol-4-yl)-2-oxo-5-phenyl-1,2,3,4-tetrahydropyrimidin-4-yl)benzoic acid;
(R)-2-hydroxy-4-(6-(1-methyl-1H-pyrazol-4-yl)-2-oxo-5-(thiophen-3-yl)-1,2,3,4-tetrahydropyrimidin-4-yl)benzoic acid;
4-(3-(2-(dimethylamino)ethoxy)-4-hydroxy-5-nitrophenyl)-5,6-diphenyl-3,4-dihydropyrimidin-2(1H)-one;
4-(3-ethoxy-4-hydroxy-5-nitrophenyl)-5-phenyl-6-(tetrahydrofuran-2-yl)-3,4-dihydropyrimidin-2(1H)-one;
6-cyclopentyl-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-5-phenyl-6-(tetrahydrofuran-3-yl)-3,4-dihydropyrimidin-2(1H)-one;
6-cyclohexyl-4-(3-ethoxy-4-hydroxy-5-nitrophenyl)-5-(thiophen-3-yl)-3,4-dihydropyrimidin-2(1H)-one;
4-(3-ethoxy-4-hydroxy-5-nitrophenyl)-5-phenyl-6-((S)-tetrahydrofuran-2-yl)-3,4-dihydropyrimidin-2(1H)-one;
4-(3-ethoxy-4-hydroxy-5-nitrophenyl)-5-phenyl-6-((R)-tetrahydrofuran-2-yl)-3,4-dihydropyrimidin-2(1H)-one; and
5-cyclohexyl-4-(3-ethoxy-4-hydroxy-5-nitrophenyl)-6-phenyl-3,4-dihydropyrimidin-2(1H)-one.

Detailed synthesis of the above molecules was described in provisional application U.S. 61/245,902 filed on Sep. 25, 2009 and PCT International Application Serial No. PCT/US10/50164 filed on Sep. 24, 2010, both incorporated herein by reference in their entirety.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

It is to be understood that isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

2. Representative Compounds

NK3 receptor antagonist activity was determined for a subset of the compounds of Formula I. A percent inhibition value at the concentration of 10 μM was determined for selected compounds in the human NK3 receptor binding assay (see Example 1 for details). The following representative compounds had about >50% inhibition at 10 μM:
4-(3-ethoxy-4-hydroxy-5-nitrophenyl)-5,6-diphenyl-3,4-dihydropyrimidin-2(1H)-one;
4-(3-ethoxy-4-hydroxy-5-nitrophenyl)-6-phenyl-5-(thiophen-2-yl)-3,4-dihydropyrimidin-2(1H)-one;
4-(3-ethoxy-4-hydroxy-5-nitrophenyl)-6-phenyl-5-(thiophen-3-yl)-3,4-dihydropyrimidin-2(1H)-one;
4-(4-hydroxy-3-methoxy-5-nitrophenyl)-5,6-diphenyl-3,4-dihydropyrimidin-2(1H)-one;
4-(3-ethoxy-4-hydroxy-5-nitrophenyl)-5-(2-fluorophenyl)-6-phenyl-3,4-dihydropyrimidin-2(1H)-one;
4-(3-ethoxy-4-hydroxy-5-nitrophenyl)-6-(3-methoxyphenyl)-5-phenyl-3,4-dihydropyrimidin-2(1H)-one;
3-(4-(3-ethoxy-4-hydroxy-5-nitrophenyl)-2-oxo-6-phenyl-1,2,3,4-tetrahydropyrimidin-5-yl)benzonitrile;
6-(4-chloro-3-fluorophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(furan-3-yl)-5-phenyl-3,4-dihydropyrimidin-2(1H)-one;
4-(3-ethoxy-4-hydroxy-5-nitrophenyl)-5-phenyl-6-(pyridin-3-yl)-3,4-dihydropyrimidin-2(1H)-one;
3-ethoxy-2-hydroxy-5-(2-oxo-5,6-diphenyl-1,2,3,4-tetrahydropyrimidin-4-yl)benzonitrile;
4-(3-ethoxy-4-hydroxy-5-nitrophenyl)-5-phenyl-6-(thiophen-2-yl)-3,4-dihydropyrimidin-2(1H)-one;
4-(3-ethoxy-4-hydroxy-5-nitrophenyl)-5-phenyl-6-(thiophen-3-yl)-3,4-dihydropyrimidin-2(1H)-one;
4-(3-ethoxy-4-hydroxy-5-nitrophenyl)-6-(pyridin-3-yl)-5-(thiophen-3-yl)-3,4-dihydropyrimidin-2(1H)-one;
4-(3-ethoxy-4-hydroxy-5-nitrophenyl)-6-(1-methyl-1H-pyrazol-4-yl)-5-(thiophen-3-yl)-3,4-dihydropyrimidin-2(1H)-one;
4-(3-ethoxy-4-hydroxy-5-nitrophenyl)-6-(1-methyl-1H-pyrazol-3-yl)-5-(thiophen-3-yl)-3,4-dihydropyrimidin-2(1H)-one;
4-(3-chloro-4-hydroxy-5-nitrophenyl)-5,6-diphenyl-3,4-dihydropyrimidin-2(1H)-one;

4-(4-hydroxy-3-(2-methoxyethoxy)-5-nitrophenyl)-5,6-diphenyl-3,4-dihydropyrimidin-2(1H)-one; and
5-cyclohexyl-4-(3-ethoxy-4-hydroxy-5-nitrophenyl)-6-phenyl-3,4-dihydropyrimidin-2(1H)-one.

A percent inhibition value at the concentration of 1 µM was determined for selected compounds in the human NK3 receptor binding assay (see Example 2). The following representative compounds had about >50% inhibition at 1 µM:

4-(4-hydroxy-3-methoxy-5-nitrophenyl)-5,6-diphenyl-3,4-dihydropyrimidin-2(1H)-one;
4-(3-ethoxy-4-hydroxy-5-nitrophenyl)-1-methyl-5,6-diphenyl-3,4-dihydropyrimidin-2(1H)-one;
4-(3-ethoxy-4-hydroxy-5-nitrophenyl)-5-(2-fluorophenyl)-6-phenyl-3,4-dihydropyrimidin-2(1H)-one;
4-(3-ethoxy-4-hydroxy-5-nitrophenyl)-6-phenyl-5-p-tolyl-3,4-dihydropyrimidin-2(1H)-one;
4-(3-ethoxy-4-hydroxy-5-nitrophenyl)-6-(3-methoxyphenyl)-5-phenyl-3,4-dihydropyrimidin-2(1H)-one;
4-(3-ethoxy-4-hydroxy-5-nitrophenyl)-6-phenyl-5-m-tolyl-3,4-dihydropyrimidin-2(1H)-one;
5-(3-chlorophenyl)-4-(3-ethoxy-4-hydroxy-5-nitrophenyl)-6-phenyl-3,4-dihydropyrimidin-2(1H)-one;
4-(3-ethoxy-4-hydroxy-5-nitrophenyl)-6-phenyl-5-o-tolyl-3,4-dihydropyrimidin-2(1H)-one;
5-(4-chlorophenyl)-4-(3-ethoxy-4-hydroxy-5-nitrophenyl)-6-phenyl-3,4-dihydropyrimidin-2(1H)-one;
5-(2-chlorophenyl)-4-(3-ethoxy-4-hydroxy-5-nitrophenyl)-6-phenyl-3,4-dihydropyrimidin-2(1H)-one;
5-(3,4-difluorophenyl)-4-(3-ethoxy-4-hydroxy-5-nitrophenyl)-6-phenyl-3,4-dihydropyrimidin-2(1H)-one;
4-(3-ethoxy-4-hydroxy-5-nitrophenyl)-6-(4-fluorophenyl)-5-phenyl-3,4-dihydropyrimidin-2(1H)-one;
6-(4-chlorophenyl)-4-(3-ethoxy-4-hydroxy-5-nitrophenyl)-5-phenyl-3,4-dihydropyrimidin-2(1H)-one;
6-(3-chlorophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-1,3-dimethyl-5,6-diphenyl-3,4-dihydropyrimidin-2(1H)-one;
6-(4-chloro-3-fluorophenyl)-4-(3-ethoxy-4-hydroxy-5-nitrophenyl)-5-phenyl-3,4-dihydropyrimidin-2(1H)-one;
6-(3-chloro-4-fluorophenyl)-4-(3-ethoxy-4-hydroxy-5-nitrophenyl)-5-phenyl-3,4-dihydropyrimidin-2(1H)-one;
6-(3,4-difluorophenyl)-4-(3-ethoxy-4-hydroxy-5-nitrophenyl)-5-phenyl-3,4-dihydropyrimidin-2(1H)-one;
6-(3,5-difluorophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(2-fluorophenyl)-5-phenyl-3,4-dihydropyrimidin-2(1H)-one;
4-(3-ethoxy-4-hydroxy-5-nitrophenyl)-3-methyl-5,6-diphenyl-3,4-dihydropyrimidin-2(1H)-one;
4-(3-ethoxy-5-fluoro-4-hydroxyphenyl)-5,6-diphenyl-3,4-dihydropyrimidin-2(1H)-one;
3-ethoxy-2-hydroxy-5-(2-oxo-5,6-diphenyl-1,2,3,4-tetrahydropyrimidin-4-yl)benzonitrile;
7-ethoxy-5-(2-oxo-5,6-diphenyl-1,2,3,4-tetrahydropyrimidin-4-yl)benzo[d]oxazol-2(3H)-one;
2-hydroxy-3-(2-oxo-5,6-diphenyl-1,2,3,4-tetrahydropyrimidin-4-yl)benzonitrile;
4-(4-hydroxy-3-nitrophenyl)-5,6-diphenyl-3,4-dihydropyrimidin-2(1H)-one;
4-(3-bromo-5-ethoxy-4-hydroxyphenyl)-5,6-diphenyl-3,4-dihydropyrimidin-2(1H)-one;
4-(3-ethoxy-4-hydroxy-5-nitrophenyl)-5-phenyl-6-(4-(trifluoromethyl)phenyl)-3,4-dihydropyrimidin-2(1H)-one;
4-(3-ethoxy-4-hydroxy-5-nitrophenyl)-5-(3-fluorophenyl)-6-phenyl-3,4-dihydropyrimidin-2(1H)-one;
4-(3-ethoxy-4-hydroxy-5-nitrophenyl)-5-(3-ethylphenyl)-6-phenyl-3,4-dihydropyrimidin-2(1H)-one;
4-ethoxy-6-(2-oxo-5,6-diphenyl-1,2,3,4-tetrahydropyrimidin-4-yl)benzo[d]oxazol-2(3H)-one;
4-(4-hydroxy-3-(2-methoxyethoxy)-5-nitrophenyl)-5,6-diphenyl-3,4-dihydropyrimidin-2(1H)-one;
6-cyclopentyl-4-(3-ethoxy-4-hydroxy-5-nitrophenyl)-5-phenyl-3,4-dihydropyrimidin-2(1H)-one; and
5-cyclohexyl-4-(3-ethoxy-4-hydroxy-5-nitrophenyl)-6-phenyl-3,4-dihydropyrimidin-2(1H)-one.

The human NK3 receptor binding assay described in Example 3 was used to determine $IC_{50}$ values for a subset of compounds of Formula I. The following NK3 receptor antagonist compounds had an $IC_{50}$ of about 1 µM or less:

(R)-4-(3-ethoxy-4-hydroxy-5-nitrophenyl)-5,6-diphenyl-3,4-dihydropyrimidin-2(1H)-one;
(R)-4-(3-ethoxy-4-hydroxy-5-nitrophenyl)-6-phenyl-5-(thiophen-3-yl)-3,4-dihydropyrimidin-2(1H)-one;
4-(3-ethoxy-4-hydroxy-5-nitrophenyl)-1-methyl-5,6-diphenyl-3,4-dihydropyrimidin-2(1H)-one;
4-(3-ethoxy-4-hydroxy-5-nitrophenyl)-6-phenyl-5-m-tolyl-3,4-dihydropyrimidin-2(1H)-one;
5-(3-chlorophenyl)-4-(3-ethoxy-4-hydroxy-5-nitrophenyl)-6-phenyl-3,4-dihydropyrimidin-2(1H)-one;
4-(3-ethoxy-4-hydroxy-5-nitrophenyl)-1,3-dimethyl-5,6-diphenyl-3,4-dihydropyrimidin-2(1H)-one;
4-(3-ethoxy-4-hydroxy-5-nitrophenyl)-3-methyl-5,6-diphenyl-3,4-dihydropyrimidin-2(1H)-one;
(R)-4-(3-ethoxy-4-hydroxy-5-nitrophenyl)-5-phenyl-6-(pyridin-3-yl)-3,4-dihydropyrimidin-2(1H)-one;
3-ethoxy-2-hydroxy-5-(2-oxo-5,6-diphenyl-1,2,3,4-tetrahydropyrimidin-4-yl)benzonitrile;
4-ethoxy-6-(2-oxo-5,6-diphenyl-1,2,3,4-tetrahydropyrimidin-4-yl)benzo[d]oxazol-2(3H)-one; and
5-cyclohexyl-4-(3-ethoxy-4-hydroxy-5-nitrophenyl)-6-phenyl-3,4-dihydropyrimidin-2(1H)-one.

The following NK3 receptor antagonist compounds had an $IC_{50}$ of about 0.1 µM or less:

4-(3-ethoxy-4-hydroxy-5-nitrophenyl)-1,3-dimethyl-5,6-diphenyl-3,4-dihydropyrimidin-2(1H)-one; and
5-cyclohexyl-4-(3-ethoxy-4-hydroxy-5-nitrophenyl)-6-phenyl-3,4-dihydropyrimidin-2(1H)-one.

In certain embodiments of the invention it has been demonstrated that racemic mixtures of the dihydropyrimidin-2(1H)-one compounds of the invention have both NK3 receptor antagonist activity as well as S-nitrosoglutathione reductase (GSNOR) inhibitor activity. In some instances when the separated enantiomers are produced, one of the enantiomers has the majority of the NK3 receptor antagonist activity and the other enantiomer is significantly less active as a NK3 receptor antagonist. The enantiomer having greater NK3 receptor antagonist activity had minimal activity as a GSNOR inhibitor, while the enantiomer that was a poor NK3 antagonist had significantly better GSNOR inhibitor activity. For example, the following Table 1 shows racemates and separated enantiomers and their activity data for NK3 and GSNOR. See provisional application U.S. 61/245,902 filed on Sep. 25, 2009 and PCT International Application Serial No. PCT/US10/50164 filed on Sep. 24, 2010, both incorporated herein by reference in their entirety, for details on GSNOR $IC_{50}$ method. See Examples 1, 2, and 3 of this application for method details for NK3% inhibition assays and NK3 $IC_{50}$ assay.

For example, Table 1 shows for three pairs of enantiomers where the enantiomer having substantially reduced GSNOR inhibitor activity has significant activity for the neurokinin receptor NK3. The racemic mixture has activity as both a GSNOR inhibitor and an NK3 receptor antagonist. The enantiomer having greater GSNOR inhibitor activity had minimal activity as an NK3 receptor antagonist.

Without being bound by theory, it is believed in some embodiments where the enantiomers of a compound of the invention are separated, the enantiomer that demonstrates significantly better NK3 activity is of the R configuration and the enantiomer which demonstrates significantly better GSNOR inhibitor activity is of the S configuration. For example, the separated enantiomer of 4-(3-ethoxy-4-hydroxy-5-nitrophenyl)-5,6-diphenyl-3,4-dihydropyrimidin-2(1H)-one which has significantly better activity as a GSNOR inhibitor, but poor NK3 activity, has been shown by X-ray crystallography to have an S configuration when crystallized with GSNOR.

Without being bound by theory, it is believed in some embodiments where the enantiomers of a compound of the invention are separated, the enantiomer that demonstrates significantly better NK3 receptor antagonist activity is of the R configuration.

context in which it is used, "about" will mean up to plus or minus 10% of the particular term.

The term "acyl" includes compounds and moieties that contain the acetyl radical ($CH_3CO$—) or a carbonyl group to which a straight or branched chain lower alkyl residue is attached.

The term "alkyl" as used herein refers to a straight or branched chain, saturated hydrocarbon having the indicated number of carbon atoms. For example, ($C_1$-$C_6$) alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein.

The term "alkenyl" as used herein refers to a straight or branched chain unsaturated hydrocarbon having the indicated number of carbon atoms and at least one double bond. Examples of a ($C_2$-$C_8$) alkenyl group include, but are not limited to, ethylene, propylene, 1-butylene, 2-butylene, isobutylene, sec-butylene, 1-pentene, 2-pentene, isopentene,

TABLE 1

| Compound | Configuration | GSNOR $IC_{50}$ (nM) | NK3, $IC_{50}$ (nM) | NK3, % inhibition @ 10 µM |
|---|---|---|---|---|
| 4-(3-ethoxy-4-hydroxy-5-nitrophenyl)-5,6-diphenyl-3,4-dihydropyrimidin-2(1H)-one | racemic | 29 | ND | 88 |
| (S)-enantiomer | S | 11 | 19000 | ND |
| (R)-enantiomer | R | 19720 | 110 | ND |
| 4-(3-ethoxy-4-hydroxy-5-nitrophenyl)-6-phenyl-5-(thiophen-3-yl)-3,4-dihydropyrimidin-2(1H)-one | racemic | 19 | ND | 97 |
| (S)-enantiomer | S | 18 | 22000 | ND |
| (R)-enantiomer | R | 1820 | 1400 | ND |
| 4-(3-ethoxy-4-hydroxy-5-nitrophenyl)-5-phenyl-6-(pyridin-3-yl)-3,4-dihydropyrimidin-2(1H)-one | racemic | 43 | ND | 92 |
| (S)-enantiomer | S | 28 | 55000 | ND |
| (R)-enantiomer | R | 6020 | 700 | ND |
| 3-ethoxy-2-hydroxy-5-(2-oxo-6-(pyridin-3-yl)-5-(thiophen-3-yl)-1,2,3,4-tetrahydropyrimidin-4-yl)benzoic acid | racemic | 150 | ND | ND |
| (S)-enantiomer | S | 67 | ND | ND |
| (R)-enantiomer | R | 3170 | ND | ND |
| 4-(3-ethoxy-4-hydroxy-5-nitrophenyl)-6-(pyridin-3-yl)-5-(thiophen-3-yl)-3,4-dihydropyrimidin-2(1H)-one | racemic | 24 | ND | 63 |
| (S)-enantiomer | S | 16 | ND | ND |
| (R)-enantiomer | R | 1900 | ND | ND |
| 3-ethoxy-2-hydroxy-5-(6-(1-methyl-1H-pyrazol-4-yl)-2-oxo-5-(thiophen-3-yl)-1,2,3,4-tetrahydropyrimidin-4-yl)benzoic acid | racemic | 27 | ND | ND |
| (S)-enantiomer | S | 13 | ND | ND |
| (R)-enantiomer | R | 580 | ND | ND |
| 4-(3-ethoxy-4-hydroxy-5-nitrophenyl)-6-(1-methyl-1H-pyrazol-3-yl)-5-(thiophen-3-yl)-3,4-dihydropyrimidin-2(1H)-one | racemic | 40 | ND | 61 |
| (S)-enantiomer | S | 35 | ND | ND |
| (R)-enantiomer | R | 31000 | ND | ND |
| 2-hydroxy-4-(6-(1-methyl-1H-pyrazol-4-yl)-2-oxo-5-(thiophen-3-yl)-1,2,3,4-tetrahydropyrimidin-4-yl)benzoic acid | racemic | 39 | ND | ND |
| (S)-enantiomer | S | 23 | ND | ND |
| (R)-enantiomer | R | 4250 | ND | ND |

ND = not determined

C. Definitions

As used herein, "about" will be understood by persons of ordinary skill in the art and will vary to some extent on the context in which it is used. If there are uses of the term which are not clear to persons of ordinary skill in the art given the 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein.

The term "alkynyl" as used herein refers to a straight or branched chain unsaturated hydrocarbon having the indicated number of carbon atoms and at least one triple bond. Examples of a ($C_2$-$C_8$) alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein.

The term "alkoxy" as used herein refers to an —O-alkyl group having the indicated number of carbon atoms. For example, a ($C_1$-$C_6$) alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aminoalkyl" as used herein, refers to an alkyl group (typically one to six carbon atoms) wherein one or more of the $C_1$-$C_6$ alkyl group's hydrogen atoms is replaced with an amine of formula —N($R^c$)$_2$, wherein each occurrence of $R^c$ is independently —H or ($C_1$-$C_6$) alkyl. Examples of aminoalkyl groups include, but are not limited to, —$CH_2NH_2$, —$CH_2CH_2NH_2$, —$CH_2CH_2CH_2NH_2$, —$CH_2CH_2CH_2CH_2NH_2$, —$CH_2CH_2CH_2CH_2CH_2NH_2$, —$CH_2CH_2CH_2CH_2CH_2CH_2NH_2$, —$CH_2CH_2CH_2N(CH_3)_2$, t-butylaminomethyl, isopropylaminomethyl and the like.

The term "aryl" as used herein refers to a 5- to 14-membered monocyclic, bicyclic or tricyclic aromatic ring system. Examples of an aryl group include phenyl and naphthyl. An aryl group can be unsubstituted or optionally substituted with one or more substituents as described herein below. Examples of aryl groups include phenyl or aryl heterocycles such as, pyrrole, furan, thiophene, thiazole, isothiazole, imidazole, triazole, tetrazole, pyrazole, oxazole, isoxazole, pyridine, pyrazine, pyridazine, and pyrimidine, and the like.

As used herein, the term "bioactivity" indicates an effect on one or more cellular or extracellular process (e.g., via binding, signaling, etc.) which can impact physiological or pathophysiological processes.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxy" or "carboxyl" means a —COOH group or carboxylic acid.

The term "$C_m$-$C_n$" means "m" number of carbon atoms to "n" number of carbon atoms. For example, the term "$C_1$-$C_6$" means one to six carbon atoms ($C_1$, $C_2$, $C_3$, $C_4$, $C_5$ or $C_6$). The term "$C_2$-$C_6$" includes two to six carbon atoms ($C_2$, $C_3$, $C_4$, $C_5$ or $C_6$). The term "$C_3$-$C_6$" includes three to six carbon atoms ($C_3$, $C_4$, $C_5$ or $C_6$).

The term "cycloalkyl" as used herein refers to a 3- to 14-membered saturated or unsaturated non-aromatic monocyclic, bicyclic or tricyclic hydrocarbon ring system. Included in this class are cycloalkyl groups which are fused to a benzene ring. Representative cycloalkyl groups include, but are not limited to, cyclopropyl, cyclobutyl, cyclobutenyl, cyclopentyl, cyclopentenyl, cyclopentadienyl, cyclohexyl, cyclohexenyl, 1,3-cyclohexadienyl, cycloheptyl, cycloheptenyl, 1,3-cycloheptadienyl, 1,4-cycloheptadienyl, -1,3,5-cycloheptatrienyl, cyclooctyl, cyclooctenyl, 1,3-cyclooctadienyl, 1,4-cyclooctadienyl, -1,3,5-cyclooctatrienyl, decahydronaphthalene, octahydronaphthalene, hexahydronaphthalene, octahydroindene, hexahydroindene, tetrahydroinden, decahydrobenzocycloheptene, octahydrobenzocycloheptene, hexahydrobenzocycloheptene, tetrahydrobenzocycloheptene, dodecahydroheptalene, decahydroheptalene, octahydroheptalene, hexahydroheptalene, and tetrahydroheptalene, (1s,3s)-bicyclo[1.1.0]butane, bicyclo[1.1.1]pentane, bicyclo[2.1.1]hexane, Bicyclo[2.2.1]heptane, bicyclo[2.2.2]octane, bicyclo[3.1.1]heptane, bicyclo[3.2.1]octane, bicyclo[3.3.1]nonane, bicyclo[3.3.2]decane, bicyclo[3.3.]undecane, bicyclo[4.2.2]decane, bicyclo[4.3.1]decane. A cycloalkyl group can be unsubstituted or optionally substituted with one or more substituents as described herein below.

The term "halogen" includes fluorine, bromine, chlorine, iodine, etc.

The term "haloalkyl," as used herein, refers to a $C_1$-$C_6$ alkyl group wherein from one or more of the $C_1$-$C_6$ alkyl group's hydrogen atom is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroalkyl," by itself or in combination with another term, means, unless otherwise stated, a stable straight or branched chain alkyl, or combinations thereof, consisting of carbon atoms and from one to three heteroatoms selected from the group consisting of O, N and S, and wherein the nitrogen and sulfur atoms may optionally be oxidized and the nitrogen heteroatom may optionally be quaternized. The heteroatom(s) O, N and S can be placed at any position of the heteroalkyl group. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, and —$CH_2$—CH=N—$OCH_3$. Up to two heteroatoms can be consecutive, such as, for example, —$CH_2$—NH—$OCH_3$. When a prefix such as ($C_2$-$C_8$) is used to refer to a heteroalkyl group, the number of carbons (2 to 8, in this example) is meant to include the heteroatoms as well. For example, a $C_2$-heteroalkyl group is meant to include, for example, —$CH_2OH$ (one carbon atom and one heteroatom replacing a carbon atom) and —$CH_2SH$.

To further illustrate the definition of a heteroalkyl group, where the heteroatom is oxygen, a heteroalkyl group can be an oxyalkyl group. For instance, ($C_2$-$C_5$) oxyalkyl is meant to include, for example —$CH_2$—O—$CH_3$ (a $C_3$-oxyalkyl group with two carbon atoms and one oxygen replacing a carbon atom), —$CH_2CH_2CH_2CH_2OH$, —$OCH_2CH_2OCH_2CH_2OH$, —$OCH_2CH(OH)CH_2OH$, and the like.

The term "heteroaryl" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thienyl, benzothienyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, quinoxalinyl and oxazolyl. A heteroaryl group can be unsubstituted or optionally substituted with one or more substituents as described herein below.

As used herein, the term "heteroatom" is meant to include oxygen (O), nitrogen (N), and sulfur (S).

As used herein, the term "heterocycle" refers to 3- to 14-membered ring systems which are either saturated, unsaturated, or aromatic, and which contains from 1 to 4 heteroatoms independently selected from nitrogen, oxygen and sulfur, and wherein the nitrogen and sulfur heteroatoms can be optionally oxidized, and the nitrogen heteroatom can be optionally quaternized, including, including monocyclic, bicyclic, and tricyclic ring systems. The bicyclic and tricyclic ring systems may encompass a heterocycle or heteroaryl fused to a benzene ring. The heterocycle can be attached via any heteroatom or carbon atom, where chemically acceptable. Heterocycles include heteroaryls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thienyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl and quinazolinyl. A heterocycle group can be unsubstituted or optionally substituted with one or more substituents as described herein below.

The term "heterocycloalkyl," by itself or in combination with other terms, represents, unless otherwise stated, cyclic versions of "heteroalkyl." Additionally, a heteroatom can occupy the position at which the heterocycle is attached to the remainder of the molecule. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "hydroxyalkyl," as used herein, refers to an alkyl group having the indicated number of carbon atoms wherein one or more of the hydrogen atoms in the alkyl group is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof.

The term "hydroxy" or "hydroxyl" includes groups with an —OH or —O$^-$.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. In some embodiments, a stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

As used herein, "antagonist" refers to an agent that downregulates (e.g., suppresses or inhibits) at least one bioactivity of a protein. An "antagonist" or an agent that "antagonizes" may be a compound which inhibits or decreases the interaction between a protein and another molecule. Potential antagonists include small molecules that interact with the receptor site and block or depress the normal response for that receptor.

As used herein, "protein" is used synonymously with "peptide," "polypeptide," or "peptide fragment". A "purified" polypeptide, protein, peptide, or peptide fragment is substantially free of cellular material or other contaminating proteins from the cell, tissue, or cell-free source from which the amino acid sequence is obtained, or substantially free from chemical precursors or other chemicals when chemically synthesized.

As used herein, "modulate" is meant to refer to an increase or decrease in the levels of a peptide or a polypeptide, or to increase or decrease the stability or activity of a peptide or a polypeptide. The term "inhibit" is meant to refer to a decrease in the levels of a peptide or a polypeptide or to decrease in the stability or activity of a peptide or a polypeptide. In preferred embodiments, the peptide which is modulated or inhibited is S-nitrosoglutathione (GSNO) or protein S-nitrosothiols (SNOs).

As used here, the terms "nitric oxide" and "NO" encompass uncharged nitric oxide and charged nitric oxide species, particularly including nitrosonium ion (NO$^+$) and nitroxyl ion (NO$^-$). The reactive form of nitric oxide can be provided by gaseous nitric oxide. Compounds having the structure X—NO$_y$, wherein X is a nitric oxide releasing, delivering or transferring moiety, including any and all such compounds which provide nitric oxide to its intended site of action in a form active for their intended purpose, and Y is 1 or 2.

As utilized herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

A "pharmaceutically acceptable salt" or "salt" of a compound of the invention is a product of the disclosed compound that contains an ionic bond, and is typically produced by reacting the disclosed compound with either an acid or a base, suitable for administering to a subject. A pharmaceutically acceptable salt can include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, K, alkali earth metal salts such as Mg or Ca, or organic amine salts.

A "pharmaceutical composition" is a formulation comprising the disclosed compounds in a form suitable for administration to a subject. A pharmaceutical composition of the invention is preferably formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Ring double bonds, as used herein, are double bonds that are formed between two adjacent ring atoms (e.g., C=C, C=N, or N=N).

Substituents for the groups referred to as alkyl, heteroalkyl, alkylene, alkenyl, alkynyl, cycloalkyl, heterocycloalkyl, cycloalkenyl and heterocycloalkenyl can be selected from a variety of groups including —OR$^{d_t}$, =O, =NR$^{d_t}$, =N—OR$^{d_t}$, —NR$^{d_t}$R$^{d_{tt}}$, —SR$^{d_t}$, -halo, —SiR$^{d_t}$R$^{d_{tt}}$R$^{d_{ttt}}$, —OC(O)R$^{d_t}$, —C(O)R$^{d_t}$, —CO$_2$R$^{d_t}$, —CONR$^{d_t}$R$^{d_{tt}}$, —OC(O)NR$^{d_t}$R$^{d_{tt}}$, —NR$^{d_{tt}}$C(O)R$^{d_t}$, —NR$^{d_{ttt}}$C(O)NR$^{d_t}$R$^{d_{tt}}$, —NR$^{d_{ttt}}$SO$_2$NR$^{d_t}$R$^{d_{tt}}$, —NR$^{d_t}$CO$_2$R$^{d_t}$, —NHC(NH$_2$)=NH, —NR$^{a_t}$C(NH$_2$)=NH, —NHC(NH$_2$)=NR$^{d_t}$, —S(O)R$^{d_t}$, —SO$_2$R$^{d_t}$, —SO$_2$NR$^{d_t}$R$^{d_{tt}}$, —NR$^{d_{ttt}}$SO$_2$R$^{d_t}$, —CN and —NO$_2$, in a number ranging from zero to three, with those groups having zero, one or two substituents being exemplary.

R$^{d_t}$, R$^{d_{tt}}$ and R$^{d_{ttt}}$ each independently refer to hydrogen, unsubstituted (C$_1$-C$_8$)alkyl, unsubstituted hetero(C$_1$-C$_8$) alkyl, unsubstituted aryl and aryl substituted with one to three substituents selected from -halo, unsubstituted alkyl, unsubstituted alkoxy, unsubstituted thioalkoxy and unsubstituted aryl (C$_1$-C$_4$)alkyl. When R$^{d_t}$ and R$^{d_{tt}}$ are attached to the same nitrogen atom, they can be combined with the nitrogen atom to form a 5-, 6- or 7-membered ring. For example, —NR$^{d_t}$R$^{d_{tt}}$ can represent 1-pyrrolidinyl or 4-morpholinyl.

Typically, an alkyl or heteroalkyl group will have from zero to three substituents, with those groups having two or fewer substituents being exemplary of the present invention. An alkyl or heteroalkyl radical can be unsubstituted or monosubstituted. In some embodiments, an alkyl or heteroalkyl radical will be unsubstituted.

Exemplary substituents for the alkyl and heteroalkyl radicals include but are not limited to —OR$^{d_t}$, =O, =NR$^{d_t}$, =N—OR$^{d_t}$, —NR$^{d_t}$R$^{d_{tt}}$, —SR$^{d_t}$, -halo, —SiR$^{d_t}$R$^{d_{tt}}$R$^{d_{ttt}}$, —OC(O)R$^{d_t}$, —C(O)R$^{d_t}$, —CO$_2$R$^{d_t}$, —CONR$^{d_t}$R$^{d_{tt}}$, —OC(O)NR$^{d_t}$R$^{d_{tt}}$, —NR$^{d_{tt}}$C(O)R$^{d_t}$, —NR$^{d_{ttt}}$C(O)NR$^{d_t}$R$^{d_{tt}}$, —NR$^{d_{ttt}}$SO$_2$NR$^{d_t}$R$^{d_{tt}}$, —NR$^{d_{tt}}$CO$_2$R$^{d_t}$, —NHC(NH$_2$)=NH, —NR$^{a_t}$C(NH$_2$)=NH, —NHC(NH$_2$)=NR$^{d_t}$, —S(O)R$^{d_t}$, —SO$_2$R$^{d_t}$, —SO$_2$NR$^{d_t}$R$^{d_{tt}}$, —NR$^{d_{ttt}}$SO$_2$R$^{d_t}$, —CN and —NO$_2$, where R$^{d_t}$, R$^{d_{tt}}$ and R$^{d_{ttt}}$ are as defined above. Typical substituents can be selected from: —OR$^{d_t}$, =O, —NR$^{d_t}$R$^{d_{tt}}$, -halo, —OC(O)R$^{d_t}$, —CO$_2$R$^{d_t}$, —C(O)NR$^{d_t}$R$^{d_{tt}}$, —OC(O)NR$^{d_t}$R$^{d_{tt}}$, —NR$^{d_{tt}}$C(O)R$^{d_t}$, —NR$^{d_{tt}}$CO$_2$R$^{d_t}$, —NR$^{d_{ttt}}$SO$_2$NR$^{d_t}$R$^{d_{tt}}$, —SO$_2$R$^{d_t}$, —SO$_2$NR$^{d_t}$R$^{d_{tt}}$, —NR$^{d_{ttt}}$SO$_2$R$^{d_t}$—CN and —NO$_2$.

Similarly, substituents for the aryl and heteroaryl groups are varied and selected from: -halo, —OR$^{e_t}$, —OC(O)R$^{e_t}$, —NR$^{e_t}$R$^{e_{tt}}$, —SR$^{e_t}$, —R$^{e_t}$, —CN, —NO$_2$, —CO$_2$R$^{e_t}$, —C(O)NR$^{e_t}$R$^{e_{tt}}$, —C(O)R$^{e_t}$, —OC(O)NR$^{e_t}$R$^{e_{tt}}$, —NR$^{e_{tt}}$C(O)R$^{e_t}$, —NR$^{e_{tt}}$CO$_2$R$^{e_t}$, —NR$^{e_{ttt}}$C(O)NR$^{e_t}$R$^{e_{tt}}$, —NR$^{e_{ttt}}$SO$_2$NR$^{e_t}$R$^{e_{tt}}$, —NHC(NH$_2$)=NH, —NR$^{e_t}$C(NH$_2$)=NH, —NH—C(NH$_2$)=NR$^{e_t}$, —S(O)R$^{e_t}$, —SO$_2$R$^{e_t}$, —SO$_2$NR$^{e_t}$R$^{e_{tt}}$, —NR$^{e_{ttt}}$SO$_2$R$^{e_t}$, —N$_3$, —CH(Ph)$_2$, perfluoroalkoxy and perfluoro(C$_1$-C$_4$)alkyl, in a number ranging from zero to the total number of open valences on the aromatic ring system.

R$^{e_t}$, R$^{e_{tt}}$ and R$^{e_{ttt}}$ are independently selected from hydrogen, unsubstituted (C$_1$-C$_8$) alkyl, unsubstituted hetero(C$_1$-C$_8$) alkyl, unsubstituted aryl, unsubstituted heteroaryl, unsubstituted aryl(C$_1$-C$_4$) alkyl and unsubstituted aryloxy (C$_1$-C$_4$) alkyl. Typically, an aryl or heteroaryl group will have from zero to three substituents, with those groups having two or fewer substituents being exemplary in the present invention. In one embodiment of the invention, an aryl or heteroaryl group will be unsubstituted or monosubstituted. In another embodiment, an aryl or heteroaryl group will be unsubstituted.

Two of the substituents on adjacent atoms of an aryl or heteroaryl ring in an aryl or heteroaryl group as described herein may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -J-(CH$_2$)$_r$—K—, wherein J and K are independently —CH$_2$—, —O—, —NH—, —S—, —S(O)—, —S(O)$_2$—, —S(O)$_2$NR$^{f_t}$— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR$^{f_t}$—, —S—, —S(O)—, —S(O)$_2$—, or —S(O)$_2$NR$^{a_t}$—. The substituent R$^{f_t}$ in —NR$^{f_t}$— and —S(O)$_2$NR$^{f_t}$— is selected from hydrogen or unsubstituted (C$_1$-C$_6$) alkyl.

"Stable compound" and "stable structure" are meant to indicate a compound that is sufficiently robust to survive isolation to a useful degree of purity from a reaction mixture, and formulation into an efficacious therapeutic agent.

As used herein the term "therapeutically effective amount" generally means the amount necessary to ameliorate at least one symptom of a disorder to be prevented, reduced, or treated as described herein. The phrase "therapeutically effective amount" as it relates to NK3 receptor antagonists of the present invention shall mean the NK3 receptor antagonist dosage that provides the specific pharmacological response for which the NK3 receptor antagonist is administered in a significant number of subjects in need of such treatment. It is emphasized that a therapeutically effective amount of a NK3 receptor antagonist that is administered to a particular subject in a particular instance will not always be effective in treating the conditions/diseases described herein, even though such dosage is deemed to be a therapeutically effective amount by those of skill in the art.

The term "biological sample" includes, but is not limited to, samples of blood (e.g., serum, plasma, or whole blood), urine, saliva, sweat, breast milk, vaginal secretions, semen, hair follicles, skin, teeth, bones, nails, or other secretions, body fluids, tissues, or cells. In accordance with the invention, the levels of the S-nitrosoglutathione reductase in the biological sample can be determined by the methods described in U.S. Patent Application Publication No. 2005/0014697.

D. Pharmaceutical Compositions

The invention encompasses pharmaceutical compositions comprising at least one compound of the invention described herein and at least one pharmaceutically acceptable carrier. Suitable carriers are described in "Remington: *The Science and Practice, Twentieth Edition*," published by Lippincott Williams & Wilkins, which is incorporated herein by reference. Pharmaceutical compositions according to the invention may also comprise one or more non-inventive compound active agents.

The pharmaceutical compositions of the invention can comprise novel compounds described herein, the pharmaceutical compositions can comprise known compounds which previously were not known to have NK3 receptor antagonist activity, or a combination thereof.

The compounds of the invention can be utilized in any pharmaceutically acceptable dosage form, including but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the compounds of the invention described herein can be formulated: (a) for administration selected from the group consisting of oral, pulmonary, intravenous, intra-arterial, intrathecal, intra-articular, rectal, ophthalmic, colonic, parenteral, intracisternal, intravaginal, intraperitoneal, local, buccal, nasal, and topical administration; (b) into a dosage form selected from the group consisting of liquid dispersions, gels, aerosols, ointments, creams, tablets, sachets and capsules; (c) into a dosage form selected from the group consisting of lyophilized formulations, dry powders, fast melt formulations, controlled release formulations, delayed release formulations, extended release formulations, pulsatile release formulations, and mixed immediate release and controlled release formulations; or (d) any combination thereof.

For respiratory infections, an inhalation formulation can be used to achieve high local concentrations. Formulations suitable for inhalation include dry power or aerosolized or vaporized solutions, dispersions, or suspensions capable of being dispensed by an inhaler or nebulizer into the endobronchial or nasal cavity of infected patients to treat upper and lower respiratory bacterial infections.

Solutions or suspensions used for parenteral, intradermal, or subcutaneous application can comprise one or more of the following components: (1) a sterile diluent such as water for injection, saline solution, fixed oils, polyethylene glycols, glycerine, propylene glycol or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use may comprise sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringability exists. The pharmaceutical composition should be stable under the conditions of manufacture and storage and should be preserved against the contaminating action of microorganisms such as bacteria and fungi.

The carrier can be a solvent or dispersion medium comprising, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent in the required amount in an appropriate solvent with one or a combination of ingredients enumerated above, as required, followed by filtered sterilization. Generally, dispersions are prepared by incorporating at least one compound of the invention into a sterile vehicle that contains a basic dispersion medium and any other required ingredients. In the case of sterile powders for the preparation of sterile injectable solutions, exemplary methods of preparation include vacuum drying and freeze-drying, both of which yield a powder of a compound of the invention plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the compound of the invention can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from pressured container or dispenser that contains a suitable propellant, e.g., a gas such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In one embodiment, the compounds of the invention are prepared with carriers that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of the compounds of the invention may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of the compound of the invention calculated to produce the desired therapeutic effect in association with the required pharmaceutical carrier. The specification for the dosage unit forms of the invention are dictated by and directly dependent on the unique characteristics of the compound of the invention and the particular therapeutic effect to be achieved, and the limitations inherent in the art of compounding such an active agent for the treatment of individuals.

Pharmaceutical compositions according to the invention comprising at least one compound of the invention can comprise one or more pharmaceutical excipients. Examples of such excipients include, but are not limited to binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, such as Avicel® PH101 and Avicel® PH102, silicified microcrystalline cellulose (ProSolv SMCC™), gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, cross-povidone, sodium starch glycolate, and mixtures thereof; (4) lubricants, including agents that act on the flowability of a powder to be compressed, include magnesium stearate, colloidal silicon dioxide, such as Aerosil® 200, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, Magnasweet® (trademark of MAFCO), bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

E. Kits Comprising the Compositions of the Invention

The present invention also encompasses kits comprising the compositions of the invention. Such kits can comprise, for example, (1) at least one compound of the invention; and (2) at least one pharmaceutically acceptable carrier, such as a solvent or solution. Additional kit components can optionally include, for example: (1) any of the pharmaceutically acceptable excipients identified herein, such as stabilizers, buffers, etc., (2) at least one container, vial or similar apparatus for holding and/or mixing the kit components; and (3) delivery apparatus, such as an inhaler, nebulizer, syringe, etc.

F. Methods of Preparing Compounds of the Invention

The compounds of the invention can readily be synthesized using known synthetic methodologies or via a modification of known synthetic methodologies. As would be readily recognized by a skilled artisan, the methodologies described below allow the synthesis of dihydropyrimidin-2(1H)-ones having a variety of substituents. Exemplary synthetic methods are described in provisional application U.S. 61/245,902 filed on Sep. 25, 2009 and PCT International Application Serial No. PCT/US10/50164 filed on Sep. 24, 2010, both incorporated herein by reference in their entirety.

If needed, further purification and separation of enantiomers and diastereomers can be achieved by routine procedures known in the art. Thus, for example, the separation of enantiomers of a compound can be achieved by the use of chiral HPLC and related chromatographic techniques. Diastereomers can be similarly separated. In some instances, however, diastereomers can simply be separated physically, such as, for example, by controlled precipitation or crystallization.

The process of the invention, when carried out as prescribed herein, can be conveniently performed at temperatures that are routinely accessible in the art. In one embodiment, the process is performed at a temperature in the range of about 25° C. to about 110° C. In another embodiment, the temperature is in the range of about 40° C. to about 100° C. In yet another embodiment, the temperature is in the range of about 50° C. to about 95° C.

Synthetic steps that require a base are carried out using any convenient organic or inorganic base. Typically, the base is not nucleophilic. Thus, in one embodiment, the base is selected from carbonates, phosphates, hydroxides, alkoxides, salts of disilazanes, and tertiary amines.

The process of the invention, when performed as described herein, can be substantially complete after several minutes to after several hours depending upon the nature and quantity of reactants and reaction temperature. The determination of when the reaction is substantially complete can be conveniently evaluated by ordinary techniques known in the art such as, for example, HPLC, LCMS, TLC, and $^1$H NMR.

G. Methods of Treatment

The invention encompasses methods of preventing or treating (e.g., alleviating one or more symptoms of) medical conditions through use of one or more of the disclosed compounds. The methods comprise administering a therapeutically effective amount of a compound of the invention to a patient in need. The compositions of the invention can also be used for prophylactic therapy.

The compound of the invention used in the methods of treatment according to the invention can be: (1) a novel compound described herein, or a pharmaceutically acceptable salt thereof, a prodrug thereof, or a metabolite thereof; (2) a compound which was known prior to the present invention, but wherein it was not known that the compound is a NK3 receptor antagonist, or a pharmaceutically acceptable salt thereof, a prodrug thereof, or a metabolite thereof; or (3) a compound which was known prior to the present invention, and wherein it was known that the compound is a NK3 receptor antagonist, but wherein it was not known that the compound is useful for the methods of treatment described herein, or a pharmaceutically acceptable salt thereof, a prodrug thereof, or a metabolite thereof.

The patient can be any animal, domestic, livestock or wild, including, but not limited to cats, dogs, horses, pigs and cattle, and preferably human patients. As used herein, the terms patient and subject may be used interchangeably.

As used herein, "treating" describes the management and care of a patient for the purpose of combating a disease, condition, or disorder and includes the administration of a compound of the present invention to prevent the onset of the symptoms or complications, alleviating the symptoms or complications, or eliminating the disease, condition or disorder. More specifically, "treating" includes reversing, attenuating, alleviating, minimizing, suppressing or halting at least one deleterious symptom or effect of a disease (disorder) state, disease progression, disease causative agent (e.g., bacteria or viruses), or other abnormal condition. Treatment is continued as long as symptoms and/or pathology ameliorate.

In general, the dosage, i.e., the therapeutically effective amount, ranges from 1 μg to 10 g/kg and often ranges from 10 μg to 1 g/kg or 10 μg to 100 mg/kg body weight of the subject being treated, per day.

The present invention provides a method of treating a subject afflicted with a disorder which is characterized by overstimulation of the tachkinin NK3 receptor. Such a method comprises administering to a subject a therapeutically effective amount of a NK3 receptor antagonist.

H. NK3 Receptor Antagonist Uses

The compounds of Formula I, particularly the active enantiomers that antagonize the NK3 receptor are useful in the prevention and treatment of a wide variety of clinical conditions which are characterized by overstimulation of the tachkinin receptors, in particular, NK1, NK2 and NK3, and most particularly NK3. These conditions may include disorders of the central nervous system (CNS) such as anxiety, depression, psychosis, and schizophrenia; neurodegenerative disorders such as AIDS related dementia, senile dementia of the Alzheimer's type, Alzheimer's disease and Down's syndrome; demyelinating diseases such as multiple sclerosis and amyotrophic lateral sclerosis and other neuropathological disorders such as diabetic or peripheral neuropathy, AIDS related neuropathy, chemotherapy-induced neuropathy, and neuralgia; respiratory diseases such as chronic obstructive airways disease, bronchopneumonia, bronchospasm and asthma; inflammatory diseases such as inflammatory bowel disease, psoriasis, fibrositis, osteoarthritis, and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczemoatoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; functional bowel disorders such as irritable bowel syndrome (IBS); disorders of bladder function; fibrosing and collagen diseases such as scleroderma and eosinophilic fascioliasis; disorders of blood flow caused by vasodilation and vasospastic diseases such as angina, migraine and Reynaud's disease; and pain or nociception, for example, that is attributable to or associated with any of the foregoing conditions especially the transmission of pain in migraine. Hence, these compounds are readily adapted to therapeutic use for the treatment of physiological disorders associated with the overstimulation of the tachykinin receptors, in particular NK1, NK2 and NK3, and most particularly NK3.

I. GSNOR Inhibitor uses

In some embodiments, the dihydropyrimidin-2(1H)-ones of the present invention are both NK3 receptor antagonists and S-nitrosoglutathione reductase (GSNOR) inhibitors. See provisional application U.S. 61/245,902 filed on Sep. 25, 2009 and PCT International Application Serial No. PCT/US10/50164 filed on Sep. 24, 2010, for details on the uses of GSNOR inhibitors.

J. Uses in an Apparatus

The compounds of the present invention or a pharmaceutically acceptable salt thereof, or a prodrug or metabolite thereof, can be applied to various apparatus in circumstances when the presence of such compounds would be beneficial. Such apparatus can be any device or container, for example, implantable devices in which a compound of the invention can be used to coat a surgical mesh or cardiovascular stent prior to implantation in a patient. The compounds of the invention can also be applied to various apparatus for in vitro assay purposes or for culturing cells.

The compounds of the present invention or a pharmaceutically acceptable salt thereof, or a prodrug or metabolite thereof, can also be used as an agent for the development, isolation or purification of binding partners to compounds of the invention, such as antibodies, natural ligands, and the like. Those skilled in the art can readily determine related uses for the compounds of the present invention.

EXAMPLES

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

Representative dihydropyrimidin-2(1H)-one analogs of Formula I useful as NK3 receptor antagonists can be prepared as described in provisional application U.S. 61/245,902 filed on Sep. 25, 2009 and PCT International Application Serial No. PCT/US10/50164 filed on Sep. 24, 2010, both incorporated herein by reference in their entirety.

Example 1

Human NK3 Receptor Binding Assay at 10 μM

Evaluation of the affinity of test compounds for the human neurokinin NK3 receptor from transfected CHO cells was performed using an antagonist radioligand binding assay. Antagonist activity was evaluated at a concentration of 10 μM for a representative subset of test compounds, and the results were expressed as the percent inhibition at that concentration.

Materials and Methods:

Receptor binding assays were performed using crude membranes prepared from CHO cells expressing human NK3 receptor. Osanetant (SR142801), a non-peptide NK3 antagonist, was used as a ligand, and SB222200 was used as a positive control reference compound. The assay was performed with cell membrane homogenates (24 μg protein) incubated for 120 min at 22° C. with 0.4 nM [$^3$H]SR142801 in the absence or presence of the test compound in a buffer containing 20 mM Hepes/NaOH (pH 7.4), 120 mM NaCl, 1 mM MnCl$_2$, 0.01% bacitracin, 0.002% aprotinin and 0.1% BSA. Following incubation, the samples were filtered rapidly under vacuum through glass fiber filters (GF/B, Packard) that had been presoaked with 0.3% PEI. The filters were rinsed several times with ice-cold 50 mM Tris/HCl using a 96-sample cell harvester (Unifilter, Packard), dried, and counted for radioactivity in a scintillation counter (Topcount, Packard) using a scintillation cocktail (Microscint 0, Packard). Each test compound was evaluated at a single concentration of 10 µM. The standard reference compound, SB222200, was tested in each experiment. Nonspecific binding was determined in the presence of 10 µM SB222200. The specific ligand binding to the receptor is defined as the difference between the total binding and the nonspecific binding. The results are expressed as a percent of control specific binding ((measured specific binding/control specific binding)×100) obtained in the presence of the test compounds.

Results: The following compounds had >50% inhibition at 10 µM:

4-(3-ethoxy-4-hydroxy-5-nitrophenyl)-5,6-diphenyl-3,4-dihydropyrimidin-2(1H)-one;
4-(3-ethoxy-4-hydroxy-5-nitrophenyl)-6-phenyl-5-(thiophen-2-yl)-3,4-dihydropyrimidin-2(1H)-one;
4-(3-ethoxy-4-hydroxy-5-nitrophenyl)-6-phenyl-5-(thiophen-3-yl)-3,4-dihydropyrimidin-2(1H)-one;
4-(4-hydroxy-3-methoxy-5-nitrophenyl)-5,6-diphenyl-3,4-dihydropyrimidin-2(1H)-one;
4-(3-ethoxy-4-hydroxy-5-nitrophenyl)-5-(2-fluorophenyl)-6-phenyl-3,4-dihydropyrimidin-2(1H)-one;
4-(3-ethoxy-4-hydroxy-5-nitrophenyl)-6-(3-methoxyphenyl)-5-phenyl-3,4-dihydropyrimidin-2(1H)-one;
3-(4-(3-ethoxy-4-hydroxy-5-nitrophenyl)-2-oxo-6-phenyl-1,2,3,4-tetrahydropyrimidin-5-yl)benzonitrile;
6-(4-chloro-3-fluorophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(furan-3-yl)-5-phenyl-3,4-dihydropyrimidin-2(1H)-one;
4-(3-ethoxy-4-hydroxy-5-nitrophenyl)-5-phenyl-6-(pyridin-3-yl)-3,4-dihydropyrimidin-2(1H)-one;
3-ethoxy-2-hydroxy-5-(2-oxo-5,6-diphenyl-1,2,3,4-tetrahydropyrimidin-4-yl)benzonitrile;
4-(3-ethoxy-4-hydroxy-5-nitrophenyl)-5-phenyl-6-(thiophen-2-yl)-3,4-dihydropyrimidin-2(1H)-one;
4-(3-ethoxy-4-hydroxy-5-nitrophenyl)-5-phenyl-6-(thiophen-3-yl)-3,4-dihydropyrimidin-2(1H)-one;
4-(3-ethoxy-4-hydroxy-5-nitrophenyl)-6-(pyridin-3-yl)-5-(thiophen-3-yl)-3,4-dihydropyrimidin-2(1H)-one;
4-(3-ethoxy-4-hydroxy-5-nitrophenyl)-6-(1-methyl-1H-pyrazol-4-yl)-5-(thiophen-3-yl)-3,4-dihydropyrimidin-2(1H)-one;
4-(3-ethoxy-4-hydroxy-5-nitrophenyl)-6-(1-methyl-1H-pyrazol-3-yl)-5-(thiophen-3-yl)-3,4-dihydropyrimidin-2(1H)-one;
4-(3-chloro-4-hydroxy-5-nitrophenyl)-5,6-diphenyl-3,4-dihydropyrimidin-2(1H)-one;
4-(4-hydroxy-3-(2-methoxyethoxy)-5-nitrophenyl)-5,6-diphenyl-3,4-dihydropyrimidin-2(1H)-one; and
5-cyclohexyl-4-(3-ethoxy-4-hydroxy-5-nitrophenyl)-6-phenyl-3,4-dihydropyrimidin-2(1H)-one.

Example 2

Human NK3 Receptor Binding Assay at 1 uM

Evaluation of the affinity of compounds for the human NK3 receptor from transfected CHO cells was performed using an antagonist radioligand binding assay. Antagonist activity was evaluated at a concentration of 1 µM for a representative subset of test compounds, and the results were expressed as the percent inhibition at that concentration.

Materials and Methods:

Receptor binding assays were performed using crude membranes prepared from CHO cells expressing human NK3 receptor. Osanetant (SR142801), a non-peptide NK3 antagonist, was used as a ligand, and SB222200 was used as a positive control reference compound. The assay was performed with cell membrane homogenates (24 µg protein) incubated for 120 min at 22° C. with 0.4 nM [$^3$H]SR142801 in the absence or presence of the test compound in a buffer containing 20 mM Hepes/NaOH (pH 7.4), 120 mM NaCl, 1 mM MnCl$_2$, 0.01% bacitracin, 0.002% aprotinin and 0.1% BSA. Following incubation, the samples were filtered rapidly under vacuum through glass fiber filters (GF/B, Packard) that had been presoaked with 0.3% PEI. The filters were rinsed several times with ice-cold 50 mM Tris/HCl using a 96-sample cell harvester (Unifilter, Packard), dried, and counted for radioactivity in a scintillation counter (Topcount, Packard) using a scintillation cocktail (Microscint 0, Packard). Each test compound was evaluated at a single concentration of 1 µM. The standard reference compound, SB222200, was tested in each experiment. Nonspecific binding was determined in the presence of 10 µM SB222200. The specific ligand binding to the receptor is defined as the difference between the total binding and the nonspecific binding. The results are expressed as a percent of control specific binding ((measured specific binding/control specific binding)×100) obtained in the presence of the test compounds.

Results: The following compounds had >50% inhibition at 1 µM:

4-(4-hydroxy-3-methoxy-5-nitrophenyl)-5,6-diphenyl-3,4-dihydropyrimidin-2(1H)-one;
4-(3-ethoxy-4-hydroxy-5-nitrophenyl)-1-methyl-5,6-diphenyl-3,4-dihydropyrimidin-2(1H)-one;
4-(3-ethoxy-4-hydroxy-5-nitrophenyl)-5-(2-fluorophenyl)-6-phenyl-3,4-dihydropyrimidin-2(1H)-one;
4-(3-ethoxy-4-hydroxy-5-nitrophenyl)-6-phenyl-5-p-tolyl-3,4-dihydropyrimidin-2(1H)-one;
4-(3-ethoxy-4-hydroxy-5-nitrophenyl)-6-(3-methoxyphenyl)-5-phenyl-3,4-dihydropyrimidin-2(1H)-one;
4-(3-ethoxy-4-hydroxy-5-nitrophenyl)-6-phenyl-5-m-tolyl-3,4-dihydropyrimidin-2(1H)-one;
5-(3-chlorophenyl)-4-(3-ethoxy-4-hydroxy-5-nitrophenyl)-6-phenyl-3,4-dihydropyrimidin-2(1H)-one;
4-(3-ethoxy-4-hydroxy-5-nitrophenyl)-6-phenyl-5-o-tolyl-3,4-dihydropyrimidin-2(1H)-one;
5-(4-chlorophenyl)-4-(3-ethoxy-4-hydroxy-5-nitrophenyl)-6-phenyl-3,4-dihydropyrimidin-2(1H)-one;
5-(2-chlorophenyl)-4-(3-ethoxy-4-hydroxy-5-nitrophenyl)-6-phenyl-3,4-dihydropyrimidin-2(1H)-one;
5-(3,4-difluorophenyl)-4-(3-ethoxy-4-hydroxy-5-nitrophenyl)-6-phenyl-3,4-dihydropyrimidin-2(1H)-one;
4-(3-ethoxy-4-hydroxy-5-nitrophenyl)-6-(4-fluorophenyl)-5-phenyl-3,4-dihydropyrimidin-2(1H)-one;
6-(4-chlorophenyl)-4-(3-ethoxy-4-hydroxy-5-nitrophenyl)-5-phenyl-3,4-dihydropyrimidin-2(1H)-one;
6-(3-chlorophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-1,3-dimethyl-5,6-diphenyl-3,4-dihydropyrimidin-2(1H)-one;
6-(4-chloro-3-fluorophenyl)-4-(3-ethoxy-4-hydroxy-5-nitrophenyl)-5-phenyl-3,4-dihydropyrimidin-2(1H)-one;
6-(3-chloro-4-fluorophenyl)-4-(3-ethoxy-4-hydroxy-5-nitrophenyl)-5-phenyl-3,4-dihydropyrimidin-2(1H)-one;

6-(3,4-difluorophenyl)-4-(3-ethoxy-4-hydroxy-5-nitrophenyl)-5-phenyl-3,4-dihydropyrimidin-2(1H)-one;
6-(3,5-difluorophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(2-fluorophenyl)-5-phenyl-3,4-dihydropyrimidin-2(1H)-one;
4-(3-ethoxy-4-hydroxy-5-nitrophenyl)-3-methyl-5,6-diphenyl-3,4-dihydropyrimidin-2(1H)-one;
4-(3-ethoxy-5-fluoro-4-hydroxyphenyl)-5,6-diphenyl-3,4-dihydropyrimidin-2(1H)-one;
3-ethoxy-2-hydroxy-5-(2-oxo-5,6-diphenyl-1,2,3,4-tetrahydropyrimidin-4-yl)benzonitrile;
7-ethoxy-5-(2-oxo-5,6-diphenyl-1,2,3,4-tetrahydropyrimidin-4-yl)benzo[d]oxazol-2(3H)-one;
2-hydroxy-3-(2-oxo-5,6-diphenyl-1,2,3,4-tetrahydropyrimidin-4-yl)benzonitrile;
4-(4-hydroxy-3-nitrophenyl)-5,6-diphenyl-3,4-dihydropyrimidin-2(1H)-one;
4-(3-bromo-5-ethoxy-4-hydroxyphenyl)-5,6-diphenyl-3,4-dihydropyrimidin-2(1H)-one;
4-(3-ethoxy-4-hydroxy-5-nitrophenyl)-5-phenyl-6-(4-(trifluoromethyl)phenyl)-3,4-dihydropyrimidin-2(1H)-one;
4-(3-ethoxy-4-hydroxy-5-nitrophenyl)-5-(3-fluorophenyl)-6-phenyl-3,4-dihydropyrimidin-2(1H)-one;
4-(3-ethoxy-4-hydroxy-5-nitrophenyl)-5-(3-ethylphenyl)-6-phenyl-3,4-dihydropyrimidin-2(1H)-one;
4-ethoxy-6-(2-oxo-5,6-diphenyl-1,2,3,4-tetrahydropyrimidin-4-yl)benzo[d]oxazol-2(3H)-one;
4-(4-hydroxy-3-(2-methoxyethoxy)-5-nitrophenyl)-5,6-diphenyl-3,4-dihydropyrimidin-2(1H)-one;
6-cyclopentyl-4-(3-ethoxy-4-hydroxy-5-nitrophenyl)-5-phenyl-3,4-dihydropyrimidin-2(1H)-one; and
5-cyclohexyl-4-(3-ethoxy-4-hydroxy-5-nitrophenyl)-6-phenyl-3,4-dihydropyrimidin-2(1H)-one.

Example 3

Human NK3 Receptor Binding Assay Determined by $IC_{50}$

Evaluation of the affinity of compounds for the human NK3 receptor from transfected CHO cells was performed using an antagonist radioligand binding assay. The antagonist activity of a representative subset of test compounds was evaluated over a range of concentrations, and the results were expressed as $IC_{50}$ values.

Materials and Methods:

Receptor binding assays were performed using crude membranes prepared from CHO cells expressing human NK3 receptor. Osanetant (SR142801), a non-peptide NK3 antagonist, was used as a ligand, and SB222200 was used as a positive control reference compound. The assay was performed with cell membrane homogenates (24 µg protein) incubated for 120 min at 22° C. with 0.4 nM [$^3$H]SR142801 in the absence or presence of the test compound in a buffer containing 20 mM Hepes/NaOH (pH 7.4), 120 mM NaCl, 1 mM $MnCl_2$, 0.01% bacitracin, 0.002% aprotinin and 0.1% BSA. Following incubation, the samples were filtered rapidly under vacuum through glass fiber filters (GF/B, Packard) that had been presoaked with 0.3% PEI. The filters were rinsed several times with ice-cold 50 mM Tris/HCl using a 96-sample cell harvester (Unifilter, Packard), dried, and counted for radioactivity in a scintillation counter (Topcount, Packard) using a scintillation cocktail (Microscint 0, Packard). For $IC_{50}$ generation, test compounds were assayed at 8 concentrations within the range of $1\times10^{-5}$ to $1\times10^{-10}$ M (10 µM to 100 pM). The standard reference compound, SB222200, was tested in each experiment. Nonspecific binding was determined in the presence of 10 µM SB222200. The specific ligand binding to the receptor is defined as the difference between the total binding and the nonspecific binding. The $IC_{50}$ values (concentration causing a half-maximal inhibition of control specific binding) and Hill coefficients (nH) were determined by non-linear regression analysis of the competition curves generated with mean replicate values using Hill equation curve fitting $(Y=D+[(A-D)/(1+(C/C_{50})^{nH})]$, where Y=specific binding, D=minimum specific binding, A=maximum specific binding, C=compound concentration, $C_{50}=IC_{50}$, and nH=slope factor). This analysis was performed using software developed at Cerep (Hill software) and validated by comparison with data generated by the commercial software SigmaPlot® 4.0 for Windows® (© 1997 by SPSS Inc.). The inhibition constants ($K_i$) were calculated using the Cheng Prusoff equation ($K_i=IC_{50}/(1+(L/K_D))$, where L=concentration of radioligand in the assay, and $K_D$=affinity of the radioligand for the receptor). A scatchard plot was used to determine the Kd.

Results: A subset of compounds was tested in this assay. The following NK3 antagonist compounds had an $IC_{50}$ of about 1 µM or less:
(R)-4-(3-ethoxy-4-hydroxy-5-nitrophenyl)-5,6-diphenyl-3,4-dihydropyrimidin-2(1H)-one;
(R)-4-(3-ethoxy-4-hydroxy-5-nitrophenyl)-6-phenyl-5-(thiophen-3-yl)-3,4-dihydropyrimidin-2(1H)-one;
4-(3-ethoxy-4-hydroxy-5-nitrophenyl)-1-methyl-5,6-diphenyl-3,4-dihydropyrimidin-2(1H)-one;
4-(3-ethoxy-4-hydroxy-5-nitrophenyl)-6-phenyl-5-m-tolyl-3,4-dihydropyrimidin-2(1H)-one;
5-(3-chlorophenyl)-4-(3-ethoxy-4-hydroxy-5-nitrophenyl)-6-phenyl-3,4-dihydropyrimidin-2(1H)-one;
4-(3-ethoxy-4-hydroxy-5-nitrophenyl)-1,3-dimethyl-5,6-diphenyl-3,4-dihydropyrimidin-2(1H)-one;
4-(3-ethoxy-4-hydroxy-5-nitrophenyl)-3-methyl-5,6-diphenyl-3,4-dihydropyrimidin-2 (1H)-one;
(R)-4-(3-ethoxy-4-hydroxy-5-nitrophenyl)-5-phenyl-6-(pyridin-3-yl)-3,4-dihydropyrimidin-2(1H)-one;
3-ethoxy-2-hydroxy-5-(2-oxo-5,6-diphenyl-1,2,3,4-tetrahydropyrimidin-4-yl)benzonitrile;
4-ethoxy-6-(2-oxo-5,6-diphenyl-1,2,3,4-tetrahydropyrimidin-4-yl)benzo[d]oxazal-2(3H)-one; and
5-cyclohexyl-4-(3-ethoxy-4-hydroxy-5-nitrophenyl)-6-phenyl-3,4-dihydropyrimidin-2 (1H)-one;

The following NK3 receptor antagonist compounds had an IC50 of about 0.1 µM or less:
4-(3-ethoxy-4-hydroxy-5-nitrophenyl)-1,3-dimethyl-5,6-diphenyl-3,4-dihydropyrimidin-2(1H)-one; and
5-cyclohexyl-4-(3-ethoxy-4-hydroxy-5-nitrophenyl)-6-phenyl-3,4-dihydropyrimidin-2(1H)-one.

Example 4

Human Neurokinin NK3 Receptor-Antagonist Effect

Experimental Model

This model evaluates the antagonist activity of compounds in CHO cells transfected with the human NK3 receptor. Antagonist activity is determined by measuring the effect of compounds on agonist-induced cytosolic $Ca^{2+}$ ion mobilization using a fluorimetric detection method.

Materials and Methods

The cells are suspended in DMEM buffer (Invitrogen) supplemented with 0.1% FCS and distributed in 96-well microplates at a density of $3\times10^4$ cells/well. The fluorescent probe (Calcium4, Molecular Device) is mixed with probenicid in HBSS buffer plus 20 mM Hepes (pH 7.4) (Invitrogen) and added into each well. The probe is allowed to equilibrate with the cells for 60 minutes at 37° C. followed by a 15 minute incubation at 22° C. Thereafter, the assay plates are positioned in a microplate reader (CellLux, PerkinElmer) and the test compound, reference antagonist or HBSS buffer is added. 5 minutes later, 1 nM [MePhe$^7$]-NKB or HBSS buffer (basal control) is added, and changes in fluorescence intensity are measured. Fluorescence intensity varies proportionally to the free cytosolic Ca2+ ion concentration, and the results are expressed as a percent inhibition of the control response to 1 nM [MePhe$^7$]-NKB.

The standard reference antagonist is SB 222200, which is tested in each experiment at several concentrations to generate a concentration-response curve from which an IC$_{50}$ value can be calculated.

REFERENCE

MEDHURST, A. D., HIRST, W. D., JERMAN, J. C., MEAKIN, J., ROBERTS, J. C., TESTA, T. and SMART, D. (1999), Molecular and pharmacological characterisation of a functional tachykinin NK3 receptor cloned from the rabbit iris sphincter muscle. Brit. J. Pharmacol., 128: 627.

Results

An antagonist effect was seen for 5-cyclohexyl-4-(3-ethoxy-4-hydroxy-5-nitrophenyl)-6-phenyl-3,4-dihydropyrimidin-2(1H)-one at 10 uM.

Example 5

Human Neurokinin NK3 Receptor-Agonist Effect

Experimental Model

This model evaluates the agonist activity of compounds in CHO cells transfected with the human NK3 receptor. Agonist activity is determined by measuring the effect of compounds on cytosolic Ca$^{2+}$ ion mobilization using a fluorimetric detection method.

Materials and Methods

The transfected CHO cells are suspended in DMEM buffer (Invitrogen) supplemented with 0.1% FCS, then distributed in 96-well microplates at a density of 3×10$^4$ cells/well. The fluorescent probe (Calcium4, Molecular Device) is mixed with probenicid in HBSS buffer plus 20 mM Hepes (pH 7.4) (Invitrogen) and added into each well. The probe is allowed to equilibrate with the cells for 60 minutes at 37° C. followed by a 15 minute incubation at 22° C. Thereafter, the assay plates are positioned in a microplate reader (CellLux, PerkinElmer) and the test compound, reference agonist or HBSS buffer (basal control) is added. Changes in fluorescence intensity, which varies proportionally to the free cytosolic Ca$^{2+}$ ion concentration, are then measured. For stimulated control measurements, [MePhe$^7$]-NKB at 10 nM is added in separate assay wells, and the results are expressed as a percent of the control response to 10 nM [MePhe$^7$]-NKB.

The standard reference agonist is [MePhe$^7$]-NKB, which is tested in each experiment at several concentrations to generate a concentration-response curve from which an EC$_{50}$ value can be calculated.

REFERENCE

MEDHURST, A. D., HIRST, W. D., JERMAN, J. C., MEAKIN, J., ROBERTS, J. C., TESTA, T. and SMART, D. (1999), Molecular and pharmacological characterisation of a functional tachykinin NK3 receptor cloned from the rabbit iris sphincter muscle. Brit. J. Pharmacol., 128: 627.

Results 5-cyclohexyl-4-(3-ethoxy-4-hydroxy-5-nitrophenyl)-6-phenyl-3,4-dihydropyrimidin-2(1H)-one was assayed for agonist effect and no effect was seen at the highest tested concentration.

It will be apparent to those skilled in the art that various modifications and variations can be made in the methods and compositions of the present invention without departing from the spirit or scope of the invention.

What is claimed is:

1. A method of attenuating at least one deleterious symptom or effect of schizophrenia characterized by overstimulation of NK3 which comprises administering to a patient in need thereof a therapeutically effective amount of an NK3 receptor antagonist of formula I:

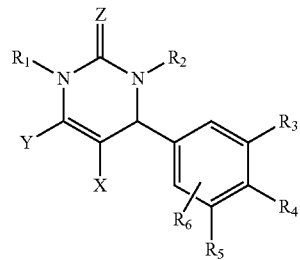

wherein
X is selected from the group consisting of aryl, substituted aryl, heteroaryl, substituted heteroaryl, cycloalkyl, substituted cycloalkyl, heterocyclyl, and substituted heterocyclyl, each having 6 members or less in the ring;
Y is selected from the group consisting of aryl, substituted aryl, heteroaryl, substituted heteroaryl, cycloalkyl, substituted cycloalkyl, heterocyclyl, and substituted heterocyclyl;
Z is selected from the group consisting of O, S and NR$_7$;
R$_1$, R$_2$ and R$_7$ are independently selected from the group consisting of hydrogen, and C$_1$-C$_6$ alkyl;
R$_3$ is selected from the group consisting of hydrogen, nitro, cyano, carboxyl, carbamoyl, methylsulfonamido, fluoro, chloro, bromo, hydroxy, methylsulfonyl, and methylsulfinyl, isoxazol-4-yl, C$_1$-C$_6$ alkoxy, —C(NH) NHOH, sulfonic acid, and acetyl;
R$_4$ is selected from the group consisting of hydrogen, hydroxy, methoxy, carboxyl, and tetrazol-5-yl;
or optionally R$_3$ and R$_4$, taken together can form a heterocycle;
R$_5$ is selected from the group consisting of hydrogen, hydroxyl, carboxy, chloro, fluoro, cyano, —O(CH$_2$)$_{1-6}$ NMe$_2$, C$_1$-C$_6$ alkyl, —O(CH$_2$)$_{1-6}$OCH$_3$, —O(CH$_2$)$_{1-6}$ OH, acetyl, CF$_3$, and C$_1$-C$_6$ alkoxy;
or optionally R$_4$ and R$_5$, taken together can form a heterocycle; and
R$_6$ is selected from the group consisting of hydrogen and hydroxyl.

2. The method of claim 1 wherein R$_1$, R$_2$ and R$_7$ are independently selected from the group consisting of hydrogen and methyl;
R$_3$ is selected from the group consisting of hydrogen, nitro, cyano, carboxyl, carbamoyl, methylsulfonamido, fluoro, chloro, bromo, methylsulfonyl, and methylsulfinyl, isoxazol-4-yl, $C_1$-$C_6$ alkoxy, —C(NH)NHOH, sulfonic acid, and acetyl;

$R_4$ is selected from the group consisting of hydroxy, carboxyl, and tetrazol-5-yl;

$R_5$ is selected from the group consisting of hydrogen, hydroxyl, carboxy, chloro, fluoro, cyano, —O(CH$_2$)$_2$NMe$_2$, $C_1$-$C_6$ alkyl, —O(CH$_2$)$_2$OCH$_3$, —O(CH$_2$)$_2$OH, acetyl, CF$_3$, methoxy, ethoxy, isopropoxy, and n-propoxy; and $R_6$ is hydrogen.

3. The method of claim 1 wherein X is selected from the group consisting of phenyl, substituted phenyl, thiophen-yl, substituted thiophen-yl, thiazol-yl, substituted thiazol-yl, pyrazin-yl, substituted pyrazin-yl, pyridin-yl, and substituted pyridin-yl, cyclohexyl, and substituted cyclohexyl.

4. The method of claim 1 wherein X is selected from the group consisting of phenyl, thiophen-2-yl, thiophen-3-yl, thiazol-2-yl, 2-fluorophenyl, p-tolyl, m-tolyl, biphenyl-4-yl, 4-methoxyphenyl, 3-chlorophenyl, 3,4-dichlorophenyl, 3-methoxyphenyl, 3,4-dimethoxyphenyl, 4-bromophenyl, o-tolyl, 4-chlorophenyl, 2-chlorophenyl, 3-cyanophenyl, 3,4-difluorophenyl, 4-cyanophenyl, 3-carbamoylphenyl, pyrazin-2-yl, biphenyl-3-yl, 2-cyanophenyl, pyridin-4-yl, and pyridin-3-yl, 4-(dimethylamino)phenyl, 3-fluorophenyl, 3-ethylphenyl, and cyclohexyl.

5. The method of claim 1 wherein Y is selected from phenyl, substituted phenyl, thiophen-yl, substituted thiophen-yl, thiazol-yl, substituted thiazol-yl, pyrazin-yl, substituted pyrazin-yl, pyridin-yl, substituted pyridin-yl, furan-yl, substituted furan-yl, benzo[d][1,3]dioxol-yl, substituted benzo[d][1,3]dioxol-yl, imidazol-yl, substituted imidazol-yl, naphthalen-yl, substituted naphthalen-yl, pyrrol-yl, substituted pyrrol-yl, pyrazol-yl, substituted pyrazol-yl, tetrahydrofuran-yl, substituted tetrahydrofuran-yl, cyclopentyl, substituted cyclopentyl, cyclohexyl, and substituted cyclohexyl.

6. The method of claim 1 wherein Y is selected from the group consisting of phenyl, 3-methoxyphenyl, p-tolyl, 4-methoxyphenyl, 3,5-dichlorophenyl, 3-fluorophenyl, 4-bromophenyl, biphenyl-4-yl, 4-fluorophenyl, 4-chlorophenyl, 3-chlorophenyl, 3,4-dimethoxyphenyl, 3-fluoro-4-methoxyphenyl, 4-chloro-3-fluorophenyl, 3-chloro-4-fluorophenyl, 3,4-difluorophenyl, 3,5-difluorophenyl, 3,4-dichlorophenyl, 4-hydroxyphenyl, 2,4-difluorophenyl, furan-3-yl, 2-chlorophenyl, 3-cyanophenyl, 4-(dimethylamino)phenyl, 2-fluorophenyl, 4-morpholinophenyl, 4-aminophenyl, naphthal-2-yl, benzo[d][1,3]dioxol-5-yl, 4-cyanophenyl, naphthal-3-yl, naphthal-4-yl, 4-acetamidophenyl, thiophen-2-yl, thiophen-3-yl, 1-methyl-1H-imidazol-4-yl, naphthalene-1-yl, methyl phenylcarbamate, and naphthalene-2-yl, 4-(methanesulfonamido)phenyl, 1H-pyrrol-3-yl, 1-(phenylsulfonyl)-1H-pyrrol-3-yl, furan-2-yl, 4-(trifluoromethyl)phenyl, o-tolyl, 1-methyl-1H-pyrazol-4-yl, 1-methyl-1H-pyrazol-3-yl, 3-chloro-5-fluorophenyl, 3-hydroxyphenyl, pyrazin-2-yl, quinolin-6-yl, isoquinolin-6-yl, 1-methyl-1H-pyrazol-5-yl, tetrahydrofuran-2-yl, cyclopentyl, tetrahydrofuran-3-yl, and cyclohexyl.

7. The method of claim 1 wherein the NK3 receptor antagonist is selected from the group consisting of 4-(3-ethoxy-4-hydroxy-5-nitrophenyl)-5,6-diphenyl-3,4-dihydropyrimidin-2(1H)-one;

(R)-4-(3-ethoxy-4-hydroxy-5-nitrophenyl)-5,6-diphenyl-3,4-dihydropyrimidin-2(1H)-one;

4-(3-ethoxy-4-hydroxy-5-nitrophenyl)-6-phenyl-5-(thiophen-2-yl)-3,4-dihydropyrimidin-2(1H)-one;

4-(3-ethoxy-4-hydroxy-5-nitrophenyl)-6-phenyl-5-(thiophen-3-yl)-3,4-dihydropyrimidin-2(1H)-one;

(R)-4-(3-ethoxy-4-hydroxy-5-nitrophenyl)-6-phenyl-5-(thiophen-3-yl)-3,4-dihydropyrimidin-2(1H)-one;

4-(3-ethoxy-4-hydroxy-5-nitrophenyl)-5,6-diphenyl-3,4-dihydropyrimidine-2(1H)-thione;

4-(4-hydroxy-3-methoxy-5-nitrophenyl)-5,6-diphenyl-3,4-dihydropyrimidin-2(1H)-one;

4-(3,4-dihydroxy-5-nitrophenyl)-5,6-diphenyl-3,4-dihydropyrimidin-2(1H)-one;

4-(3-ethoxy-4-hydroxy-5-nitrophenyl)-1-methyl-5,6-diphenyl-3,4-dihydropyrimidin-2(1H)-one;

4-(3-ethoxy-4-hydroxy-5-nitrophenyl)-6-phenyl-5-(thiazol-2-yl)-3,4-dihydropyrimidin-2(1H)-one;

4-(3-ethoxy-4-hydroxy-5-nitrophenyl)-5-(2-fluorophenyl)-6-phenyl-3,4-dihydropyrimidin-2(1H)-one;

4-(3-ethoxy-4-hydroxy-5-nitrophenyl)-6-phenyl-5-p-tolyl-3,4-dihydropyrimidin-2(1H)-one;

4-(3-ethoxy-4-hydroxy-5-nitrophenyl)-6-(3-methoxyphenyl)-5-phenyl-3,4-dihydropyrimidin-2(1H)-one;

4-(3-ethoxy-4-hydroxy-5-nitrophenyl)-5-phenyl-6-p-tolyl-3,4-dihydropyrimidin-2(1H)-one;

4-(3-ethoxy-4-hydroxy-5-nitrophenyl)-6-phenyl-5-m-tolyl-3,4-dihydropyrimidin-2(1H)-one;

5-(biphenyl-4-yl)-4-(3-ethoxy-4-hydroxy-5-nitrophenyl)-6-phenyl-3,4-dihydropyrimidin-2(1H)-one;

4-(3-ethoxy-4-hydroxy-5-nitrophenyl)-5-(4-methoxyphenyl)-6-phenyl-3,4-dihydropyrimidin-2(1H)-one;

4-(3-ethoxy-4-hydroxy-5-nitrophenyl)-6-(4-methoxyphenyl)-5-phenyl-3,4-dihydropyrimidin-2(1H)-one;

5-(3-chlorophenyl)-4-(3-ethoxy-4-hydroxy-5-nitrophenyl)-6-phenyl-3,4-dihydropyrimidin-2(1H)-one;

5-(3,4-dichlorophenyl)-4-(3-ethoxy-4-hydroxy-5-nitrophenyl)-6-phenyl-3,4-dihydropyrimidin-2(1H)-one;

4-(3-ethoxy-4-hydroxy-5-nitrophenyl)-5-(3-methoxyphenyl)-6-phenyl-3,4-dihydropyrimidin-2(1H)-one;

5-(3,4-dimethoxyphenyl)-4-(3-ethoxy-4-hydroxy-5-nitrophenyl)-6-phenyl-3,4-dihydropyrimidin-2(1H)-one;

5-(4-bromophenyl)-4-(3-ethoxy-4-hydroxy-5-nitrophenyl)-6-phenyl-3,4-dihydropyrimidin-2(1H)-one;

4-(3-ethoxy-4-hydroxy-5-nitrophenyl)-6-phenyl-5-o-tolyl-3,4-dihydropyrimidin-2(1H)-one;

5-(4-chlorophenyl)-4-(3-ethoxy-4-hydroxy-5-nitrophenyl)-6-phenyl-3,4-dihydropyrimidin-2(1H)-one;

5-(2-chlorophenyl)-4-(3-ethoxy-4-hydroxy-5-nitrophenyl)-6-phenyl-3,4-dihydropyrimidin-2(1H)-one;

3-(4-(3-ethoxy-4-hydroxy-5-nitrophenyl)-2-oxo-6-phenyl-1,2,3,4-tetrahydropyrimidin-5-yl)benzonitrile;

5-(3,4-difluorophenyl)-4-(3-ethoxy-4-hydroxy-5-nitrophenyl)-6-phenyl-3,4-dihydropyrimidin-2(1H)-one;

6-(3,5-dichlorophenyl)-4-(3-ethoxy-4-hydroxy-5-nitrophenyl)-5-phenyl-3,4-dihydropyrimidin-2(1H)-one;

4-(3-ethoxy-4-hydroxy-5-nitrophenyl)-6-(3-fluorophenyl)-5-phenyl-3,4-dihydropyrimidin-2(1H)-one;

6-(4-bromophenyl)-4-(3-ethoxy-4-hydroxy-5-nitrophenyl)-5-phenyl-3,4-dihydropyrimidin-2(1H)-one;

6-(biphenyl-4-yl)-4-(3-ethoxy-4-hydroxy-5-nitrophenyl)-5-phenyl-3,4-dihydropyrimidin-2(1H)-one;

4-(3-ethoxy-4-hydroxy-5-nitrophenyl)-6-(4-fluorophenyl)-5-phenyl-3,4-dihydropyrimidin-2(1H)-one;

6-(4-chlorophenyl)-4-(3-ethoxy-4-hydroxy-5-nitrophenyl)-5-phenyl-3,4-dihydropyrimidin-2(1H)-one;

6-(3-chlorophenyl)-4-(3-ethoxy-4-hydroxy-5-nitrophenyl)-5-phenyl-3,4-dihydropyrimidin-2(1H)-one;

6-(3,4-dimethoxyphenyl)-4-(3-ethoxy-4-hydroxy-5-nitrophenyl)-5-phenyl-3,4-dihydropyrimidin-2(1H)-one;

4-(3-ethoxy-4-hydroxy-5-nitrophenyl)-6-(3-fluoro-4-methoxyphenyl)-5-phenyl-3,4-dihydropyrimidin-2(1H)-one;
4-(3-fluoro-5-hydroxy-4-methoxyphenyl)-5,6-diphenyl-3,4-dihydropyrimidin-2(1H)-one;
4-(3-ethoxy-4-hydroxy-5-nitrophenyl)-1,3-dimethyl-5,6-diphenyl-3,4-dihydropyrimidin-2(1H)-one;
4-(4-(3-ethoxy-4-hydroxy-5-nitrophenyl)-2-oxo-6-phenyl-1,2,3,4-tetrahydropyrimidin-5-yl)benzonitrile;
6-(4-chloro-3-fluorophenyl)-4-(3-ethoxy-4-hydroxy-5-nitrophenyl)-5-phenyl-3,4-dihydropyrimidin-2(1H)-one;
6-(3-chloro-4-fluorophenyl)-4-(3-ethoxy-4-hydroxy-5-nitrophenyl)-5-phenyl-3,4-dihydropyrimidin-2(1H)-one;
6-(3,4-difluorophenyl)-4-(3-ethoxy-4-hydroxy-5-nitrophenyl)-5-phenyl-3,4-dihydropyrimidin-2(1H)-one;
6-(3,5-difluorophenyl)-4-(3-ethoxy-4-hydroxy-5-nitrophenyl)-5-phenyl-3,4-dihydropyrimidin-2(1H)-one;
6-(3,4-dichlorophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(4-hydroxyphenyl)-5-phenyl-3,4-dihydropyrimidin-2(1H)-one;
6-(2,4-difluorophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(furan-3-yl)-5-phenyl-3,4-dihydropyrimidin-2(1H)-one;
6-(2-chlorophenyl)-4-(3-ethoxy-4-hydroxy-5-nitrophenyl)-5-phenyl-3,4-dihydropyrimidin-2(1H)-one;
3-(4-(3-ethoxy-4-hydroxy-5-nitrophenyl)-2-oxo-6-phenyl-1,2,3,4-tetrahydropyrimidin-5-yl)benzamide;
3-(6-(3-ethoxy-4-hydroxy-5-nitrophenyl)-2-oxo-5-phenyl-1,2,3,6-tetrahydropyrimidin-4-yl)benzonitrile;
6-(4-(dimethylamino)phenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(2-fluorophenyl)-5-phenyl-3,4-dihydropyrimidin-2(1H)-one;
4-(3-ethoxy-4-hydroxy-5-nitrophenyl)-6-(4-morpholinophenyl)-5-phenyl-3,4-dihydropyrimidin-2(1H)-one;
6-(4-aminophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-phenyl-5-(pyrazin-2-yl)-3,4-dihydropyrimidin-2(1H)-one;
4-(3-ethoxy-4-hydroxy-5-nitrophenyl)-5-phenyl-6-(pyridin-2-yl)-3,4-dihydropyrimidin-2(1H)-one;
5-(biphenyl-3-yl)-4-(3-ethoxy-4-hydroxy-5-nitrophenyl)-6-phenyl-3,4-dihydropyrimidin-2(1H)-one;
6-(benzo[d][1,3]dioxol-5-yl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-3-methyl-5,6-diphenyl-3,4-dihydropyrimidin-2(1H)-one;
4-(6-(3-ethoxy-4-hydroxy-5-nitrophenyl)-2-oxo-5-phenyl-1,2,3,6-tetrahydropyrimidin-4-yl)benzonitrile;
4-(3-ethoxy-5-fluoro-4-hydroxyphenyl)-5,6-diphenyl-3,4-dihydropyrimidin-2(1H)-one;
4-(3-ethoxy-4-hydroxy-5-nitrophenyl)-5-phenyl-6-(pyridin-3-yl)-3,4-dihydropyrimidin-2(1H)-one;
(R)-4-(3-ethoxy-4-hydroxy-5-nitrophenyl)-5-phenyl-6-(pyridin-3-yl)-3,4-dihydropyrimidin-2(1H)-one;
4-(3-fluoro-4-hydroxy-5-methoxyphenyl)-5,6-diphenyl-3,4-dihydropyrimidin-2(1H)-one;
3-ethoxy-2-hydroxy-5-(2-oxo-5,6-diphenyl-1,2,3,4-tetrahydropyrimidin-4-yl)benzonitrile;
2-(4-(3-ethoxy-4-hydroxy-5-nitrophenyl)-2-oxo-6-phenyl-1,2,3,4-tetrahydropyrimidin-5-yl)benzonitrile;

4-(3-ethoxy-4-hydroxy-5-nitrophenyl)-5-phenyl-6-(pyridin-4-yl)-3,4-dihydropyrimidin-2(1H)-one;
7-ethoxy-5-(2-oxo-5,6-diphenyl-1,2,3,4-tetrahydropyrimidin-4-yl)benzo[d]oxazol-2(3H)-one;
N-(4-(6-(3-ethoxy-4-hydroxy-5-nitrophenyl)-2-oxo-5-phenyl-1,2,3,6-tetrahydropyrimidin-4-yl)phenyl)acetamide;
4-(3-ethoxy-4-hydroxy-5-nitrophenyl)-6-phenyl-5-(pyridin-4-yl)-3,4-dihydropyrimidin-2(1H)-one;
N-(3-ethoxy-2-hydroxy-5-(2-oxo-5,6-diphenyl-1,2,3,4-tetrahydropyrimidin-4-yl)phenyl)methanesulfonamide;
N-(2-hydroxy-3-methoxy-5-(2-oxo-5,6-diphenyl-1,2,3,4-tetrahydropyrimidin-4-yl)phenyl)methanesulfonamide;
3-ethoxy-2-hydroxy-5-(2-oxo-5,6-diphenyl-1,2,3,4-tetrahydropyrimidin-4-yl)benzoic acid;
4-(3-ethoxy-4-hydroxy-5-nitrophenyl)-5-phenyl-6-(thiophen-2-yl)-3,4-dihydropyrimidin-2(1H)-one;
4-(3-ethoxy-4-hydroxy-5-nitrophenyl)-5-phenyl-6-(thiophen-3-yl)-3,4-dihydropyrimidin-2(1H)-one;
4-(3-ethoxy-4-hydroxy-5-nitrophenyl)-6-(1-methyl-1H-imidazol-4-yl)-5-phenyl-3,4-dihydropyrimidin-2(1H)-one;
4-(3-ethoxy-4-hydroxy-5-nitrophenyl)-6-(naphthalen-1-yl)-5-phenyl-3,4-dihydropyrimidin-2(1H)-one;
3-ethoxy-2-hydroxy-5-(2-oxo-5,6-diphenyl-1,2,3,4-tetrahydropyrimidin-4-yl)benzamide;
methyl 4-(6-(3-ethoxy-4-hydroxy-5-nitrophenyl)-2-oxo-5-phenyl-1,2,3,6-tetrahydropyrimidin-4-yl)phenylcarbamate;
4-(3-ethoxy-4-hydroxy-5-nitrophenyl)-6-phenyl-5-(pyridin-3-yl)-3,4-dihydropyrimidin-2(1H)-one;
4-(3-ethoxy-4-hydroxy-5-nitrophenyl)-6-(naphthalen-2-yl)-5-phenyl-3,4-dihydropyrimidin-2(1H)-one;
2-hydroxy-5-(2-oxo-5,6-diphenyl-1,2,3,4-tetrahydropyrimidin-4-yl)benzoic acid;
4-(4-hydroxy-3-methoxyphenyl)-5,6-diphenyl-3,4-dihydropyrimidin-2(1H)-one;
5-(4-(dimethylamino)phenyl)-4-(3-ethoxy-4-hydroxy-5-nitrophenyl)-6-phenyl-3,4-dihydropyrimidin-2(1H)-one;
4-(8-nitro-2,3-dihydrobenzo[b][1,4]dioxin-6-yl)-5,6-diphenyl-3,4-dihydropyrimidin-2(1H)-one;
4-(2-oxo-5,6-diphenyl-1,2,3,4-tetrahydropyrimidin-4-yl)benzoic acid;
4-(3-(isoxazol-4-yl)phenyl)-5,6-diphenyl-3,4-dihydropyrimidin-2(1H)-one;
1,1'-(2-hydroxy-5-(2-oxo-5,6-diphenyl-1,2,3,4-tetrahydropyrimidin-4-yl)-1,3-phenylene)diethanone;
3-(2-oxo-5,6-diphenyl-1,2,3,4-tetrahydropyrimidin-4-yl)benzoic acid;
2-hydroxy-3-(2-oxo-5,6-diphenyl-1,2,3,4-tetrahydropyrimidin-4-yl)benzonitrile;
4-(4-hydroxy-3-nitrophenyl)-5,6-diphenyl-3,4-dihydropyrimidin-2(1H)-one;
2-hydroxy-5-(2-oxo-5,6-diphenyl-1,2,3,4-tetrahydropyrimidin-4-yl)benzonitrile;
2-ethoxy-4-(2-oxo-5,6-diphenyl-1,2,3,4-tetrahydropyrimidin-4-yl)benzoic acid;
3-(2-oxo-5,6-diphenyl-1,2,3,4-tetrahydropyrimidin-4-yl)benzamide;
N-hydroxy-3-(2-oxo-5,6-diphenyl-1,2,3,4-tetrahydropyrimidin-4-yl)benzimidamide;
4-(3-bromo-5-ethoxy-4-hydroxyphenyl)-5,6-diphenyl-3,4-dihydropyrimidin-2(1H)-one;
N-(4-(6-(3-ethoxy-4-hydroxy-5-nitrophenyl)-2-oxo-5-phenyl-1,2,3,6-tetrahydropyrimidin-4-yl)phenyl)methanesulfonamide;

4-(4-hydroxy-3-isopropoxy-5-nitrophenyl)-5,6-diphenyl-3,4-dihydropyrimidin-2(1H)-one;
4-(3-ethoxy-4-hydroxy-5-(methylsulfonyl)phenyl)-5,6-diphenyl-3,4-dihydropyrimidin-2(1H)-one;
4-(3-ethoxy-4-hydroxy-5-(methylsulfinyl)phenyl)-5,6-diphenyl-3,4-dihydropyrimidin-2(1H)-one;
3-ethoxy-2-hydroxy-5-(2-oxo-6-phenyl-5-(thiophen-3-yl)-1,2,3,4-tetrahydropyrimidin-4-yl)benzonitrile;
4-(3-ethoxy-4-hydroxy-5-nitrophenyl)-5-phenyl-6-(1H-pyrrol-3-yl)-3,4-dihydropyrimidin-2(1H)-one;
4-(3-ethoxy-4-hydroxy-5-nitrophenyl)-5-phenyl-6-(1-(phenylsulfonyl)-1H-pyrrol-3-yl)-3,4-dihydropyrimidin-2(1H)-one;
4-(3-ethoxy-4-hydroxy-5-nitrophenyl)-6-(4-fluorophenyl)-5-(3-methoxyphenyl)-3,4-dihydropyrimidin-2(1H)-one;
4-(3-ethoxy-4-hydroxy-5-nitrophenyl)-6-(4-fluorophenyl)-5-(thiophen-3-yl)-3,4-dihydropyrimidin-2(1H)-one;
2-hydroxy-3-nitro-5-(2-oxo-5,6-diphenyl-1,2,3,4-tetrahydropyrimidin-4-yl)benzoic acid;
4-(3-ethoxy-4-hydroxy-5-nitrophenyl)-6-(furan-2-yl)-5-phenyl-3,4-dihydropyrimidin-2(1H)-one;
2-ethoxy-4-(2-imino-5,6-diphenyl-1,2,3,4-tetrahydropyrimidin-4-yl)-6-nitrophenol;
4-(3-ethoxy-4-hydroxy-5-nitrophenyl)-5-phenyl-6-(4-(trifluoromethyl)phenyl)-3,4-dihydropyrimidin-2(1H)-one;
4-(3-ethoxy-4-hydroxy-5-nitrophenyl)-5-phenyl-6-o-tolyl-3,4-dihydropyrimidin-2(1H)-one;
4-(3-ethoxy-4-hydroxy-5-nitrophenyl)-5-(3-fluorophenyl)-6-phenyl-3,4-dihydropyrimidin-2(1H)-one;
4-(3-ethoxy-4-hydroxy-5-nitrophenyl)-6-(pyridin-3-yl)-5-(thiophen-3-yl)-3,4-dihydropyrimidin-2(1H)-one;
(Z)-2-ethoxy-4-(2-(methylimino)-5,6-diphenyl-1,2,3,4-tetrahydropyrimidin-4-yl)-6-nitrophenol;
4-(3-ethoxy-4-hydroxy-5-nitrophenyl)-6-(1-methyl-1H-pyrazol-4-yl)-5-(thiophen-3-yl)-3,4-dihydropyrimidin-2(1H)-one;
4-(3-ethoxy-4-hydroxy-5-nitrophenyl)-6-(1-methyl-1H-pyrazol-3-yl)-5-(thiophen-3-yl)-3,4-dihydropyrimidin-2(1H)-one;
4-(3-chloro-4-hydroxy-5-nitrophenyl)-5,6-diphenyl-3,4-dihydropyrimidin-2(1H)-one;
6-(3-chloro-5-fluorophenyl)-4-(3-ethoxy-4-hydroxy-5-nitrophenyl)-5-phenyl-3,4-dihydropyrimidin-2(1H)-one;
2-hydroxy-3-nitro-5-(2-oxo-5,6-diphenyl-1,2,3,4-tetrahydropyrimidin-4-yl)benzonitrile;
2-hydroxy-5-(2-oxo-5,6-diphenyl-1,2,3,4-tetrahydropyrimidin-4-yl)benzenesulfonic acid;
(R)-3-ethoxy-2-hydroxy-5-(2-oxo-6-(pyridin-3-yl)-5-(thiophen-3-yl)-1,2,3,4-tetrahydropyrimidin-4-yl)benzoic acid;
3-ethoxy-2-hydroxy-5-(2-oxo-6-(pyridin-3-yl)-5-(thiophen-3-yl)-1,2,3,4-tetrahydropyrimidin-4-yl)benzoic acid;
4-(3-fluoro-4-hydroxy-5-nitrophenyl)-5,6-diphenyl-3,4-dihydropyrimidin-2(1H)-one;
3-ethoxy-2-hydroxy-5-(2-oxo-6-(pyridin-3-yl)-5-(thiophen-3-yl)-1,2,3,4-tetrahydropyrimidin-4-yl)benzonitrile;
4-(3-ethoxy-4-hydroxy-5-nitrophenyl)-6-(3-hydroxyphenyl)-5-phenyl-3,4-dihydropyrimidin-2(1H)-one;
4-(4-hydroxy-3-nitro-5-propoxyphenyl)-5,6-diphenyl-3,4-dihydropyrimidin-2(1H)-one;
4-(3-ethoxy-4-hydroxy-5-nitrophenyl)-6-(pyrazin-2-yl)-5-(thiophen-3-yl)-3,4-dihydropyrimidin-2(1H)-one;
4-(3-ethoxy-4-hydroxy-5-nitrophenyl)-5-phenyl-6-(quinolin-6-yl)-3,4-dihydropyrimidin-2(1H)-one;
4-(3-ethoxy-4-hydroxy-5-nitrophenyl)-6-(isoquinolin-6-yl)-5-phenyl-3,4-dihydropyrimidin-2(1H)-one;
4-(3-ethoxy-4-hydroxy-5-nitrophenyl)-5-(3-methoxyphenyl)-6-(pyridin-3-yl)-3,4-dihydropyrimidin-2(1H)-one;
3-ethoxy-2-hydroxy-5-(5-(3-methoxyphenyl)-2-oxo-6-(pyridin-3-yl)-1,2,3,4-tetrahydropyrimidin-4-yl)benzoic acid;
4-(3-ethoxy-4-hydroxy-5-nitrophenyl)-6-(pyridin-4-yl)-5-(thiophen-3-yl)-3,4-dihydropyrimidin-2(1H)-one;
4-(4-hydroxy-3-(2-hydroxyethoxy)-5-nitrophenyl)-5,6-diphenyl-3,4-dihydropyrimidin-2(1H)-one;
2-hydroxy-4-(2-oxo-5,6-diphenyl-1,2,3,4-tetrahydropyrimidin-4-yl)benzoic acid;
4-(3-ethoxy-4-hydroxy-5-nitrophenyl)-6-(1-methyl-1H-pyrazol-5-yl)-5-(thiophen-3-yl)-3,4-dihydropyrimidin-2(1H)-one;
2-nitro-4-(2-oxo-5,6-diphenyl-1,2,3,4-tetrahydropyrimidin-4-yl)benzoic acid;
4-(3-ethoxy-4-hydroxy-5-nitrophenyl)-5-(3-ethylphenyl)-6-phenyl-3,4-dihydropyrimidin-2(1H)-one;
3-ethoxy-2-hydroxy-5-(6-(1-methyl-1H-pyrazol-4-yl)-2-oxo-5-(thiophen-3-yl)-1,2,3,4-tetrahydropyrimidin-4-yl)benzoic acid;
(R)-4-(3-ethoxy-4-hydroxy-5-nitrophenyl)-6-(pyridin-3-yl)-5-(thiophen-3-yl)-3,4-dihydropyrimidin-2(1H)-one;
2-chloro-4-(2-oxo-5,6-diphenyl-1,2,3,4-tetrahydropyrimidin-4-yl)benzoic acid;
(R)-3-ethoxy-2-hydroxy-5-(6-(1-methyl-1H-pyrazol-4-yl)-2-oxo-5-(thiophen-3-yl)-1,2,3,4-tetrahydropyrimidin-4-yl)benzoic acid;
(R)-4-(3-ethoxy-4-hydroxy-5-nitrophenyl)-6-(1-methyl-1H-pyrazol-3-yl)-5-(thiophen-3-yl)-3,4-dihydropyrimidin-2(1H)-one;
4-ethoxy-6-(2-oxo-5,6-diphenyl-1,2,3,4-tetrahydropyrimidin-4-yl)benzo[d]oxazol-2(3H)-one;
3-fluoro-2-hydroxy-5-(2-oxo-5,6-diphenyl-1,2,3,4-tetrahydropyrimidin-4-yl)benzoic acid;
2-fluoro-4-(2-oxo-5,6-diphenyl-1,2,3,4-tetrahydropyrimidin-4-yl)benzoic acid;
2-ethoxy-6-nitro-4-(2-oxo-5,6-diphenyl-1,2,3,4-tetrahydropyrimidin-4-yl)benzoic acid;
4-(4-hydroxy-3-nitro-5-(trifluoromethyl)phenyl)-5,6-diphenyl-3,4-dihydropyrimidin-2(1H)-one;
4-(4-hydroxy-3-(2-methoxyethoxy)-5-nitrophenyl)-5,6-diphenyl-3,4-dihydropyrimidin-2(1H)-one;
4-(4-hydroxy-3-nitro-5-propylphenyl)-5,6-diphenyl-3,4-dihydropyrimidin-2(1H)-one;
4-(2-oxo-5,6-diphenyl-1,2,3,4-tetrahydropyrimidin-4-yl)-2-(trifluoromethyl)benzoic acid;
2-fluoro-6-hydroxy-4-(2-oxo-5,6-diphenyl-1,2,3,4-tetrahydropyrimidin-4-yl)benzoic acid;
2-hydroxy-4-(6-(1-methyl-1H-pyrazol-4-yl)-2-oxo-5-(thiophen-3-yl)-1,2,3,4-tetrahydropyrimidin-4-yl)benzoic acid;
2-hydroxy-4-(2-oxo-5-phenyl-6-(pyridin-3-yl)-1,2,3,4-tetrahydropyrimidin-4-yl)benzoic acid;
2-ethoxy-6-hydroxy-4-(2-oxo-5,6-diphenyl-1,2,3,4-tetrahydropyrimidin-4-yl)benzoic acid;
4-(4-(2H-tetrazol-5-yl)phenyl)-5-phenyl-6-(pyridin-3-yl)-3,4-dihydropyrimidin-2(1H)-one;
2-chloro-6-hydroxy-4-(2-oxo-5,6-diphenyl-1,2,3,4-tetrahydropyrimidin-4-yl)benzoic acid;

4-(4-(2H-tetrazol-5-yl)phenyl)-5,6-diphenyl-3,4-dihydropyrimidin-2(1H)-one;
2-hydroxy-6-methoxy-4-(2-oxo-5,6-diphenyl-1,2,3,4-tetrahydropyrimidin-4-yl)benzoic acid;
4-(4-(2H-tetrazol-5-yl)phenyl)-6-(pyridin-3-yl)-5-(thiophen-3-yl)-3,4-dihydropyrimidin-2(1H)-one;
2-hydroxy-4-(6-(1-methyl-1H-pyrazol-4-yl)-2-oxo-5-phenyl-1,2,3,4-tetrahydropyrimidin-4-yl)benzoic acid;
(R)-2-hydroxy-4-(6-(1-methyl-1H-pyrazol-4-yl)-2-oxo-5-(thiophen-3-yl)-1,2,3,4-tetrahydropyrimidin-4-yl)benzoic acid;
4-(3-(2-(dimethylamino)ethoxy)-4-hydroxy-5-nitrophenyl)-5,6-diphenyl-3,4-dihydropyrimidin-2(1H)-one;
4-(3-ethoxy-4-hydroxy-5-nitrophenyl)-5-phenyl-6-(tetrahydrofuran-2-yl)-3,4-dihydropyrimidin-2(1H)-one;
6-cyclopentyl-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-5-phenyl-6-(tetrahydrofuran-3-yl)-3,4-dihydropyrimidin-2(1H)-one;
6-cyclohexyl-4-(3-ethoxy-4-hydroxy-5-nitrophenyl)-5-(thiophen-3-yl)-3,4-dihydropyrimidin-2(1H)-one;
4-(3-ethoxy-4-hydroxy-5-nitrophenyl)-5-phenyl-6-((S)-tetrahydrofuran-2-yl)-3,4-dihydropyrimidin-2(1H)-one;
4-(3-ethoxy-4-hydroxy-5-nitrophenyl)-5-phenyl-6-((R)-tetrahydrofuran-2-yl)-3,4-dihydropyrimidin-2(1H)-one; and
5-cyclohexyl-4-(3-ethoxy-4-hydroxy-5-nitrophenyl)-6-phenyl-3,4-dihydropyrimidin-2(1H)-one.

8. The method of claim 1 wherein the NK3 receptor antagonist is selected from an R enantiomer of the compound of formula I or a pharmaceutically acceptable salt thereof.

9. The method of claim 1 wherein the NK3 receptor antagonist is selected from the group consisting of:
4-(3-ethoxy-4-hydroxy-5-nitrophenyl)-5,6-diphenyl-3,4-dihydropyrimidin-2(1H)-one;
(R)-4-(3-ethoxy-4-hydroxy-5-nitrophenyl)-5,6-diphenyl-3,4-dihydropyrimidin-2(1H)-one;
4-(3-ethoxy-4-hydroxy-5-nitrophenyl)-6-phenyl-5-(thiophen-2-yl)-3,4-dihydropyrimidin-2(1H)-one;
4-(3-ethoxy-4-hydroxy-5-nitrophenyl)-6-phenyl-5-(thiophen-3-yl)-3,4-dihydropyrimidin-2(1H)-one;
(R)-4-(3-ethoxy-4-hydroxy-5-nitrophenyl)-6-phenyl-5-(thiophen-3-yl)-3,4-dihydropyrimidin-2(1H)-one;
4-(4-hydroxy-3-methoxy-5-nitrophenyl)-5,6-diphenyl-3,4-dihydropyrimidin-2(1H)-one;
4-(3-ethoxy-4-hydroxy-5-nitrophenyl)-1-methyl-5,6-diphenyl-3,4-dihydropyrimidin-2(1H)-one;
4-(3-ethoxy-4-hydroxy-5-nitrophenyl)-5-(2-fluorophenyl)-6-phenyl-3,4-dihydropyrimidin-2(1H)-one;
4-(3-ethoxy-4-hydroxy-5-nitrophenyl)-6-phenyl-5-p-tolyl-3,4-dihydropyrimidin-2(1H)-one;
4-(3-ethoxy-4-hydroxy-5-nitrophenyl)-6-(3-methoxyphenyl)-5-phenyl-3,4-dihydropyrimidin-2(1H)-one;
4-(3-ethoxy-4-hydroxy-5-nitrophenyl)-6-phenyl-5-m-tolyl-3,4-dihydropyrimidin-2(1H)-one;
5-(3-chlorophenyl)-4-(3-ethoxy-4-hydroxy-5-nitrophenyl)-6-phenyl-3,4-dihydropyrimidin-2(1H)-one;
4-(3-ethoxy-4-hydroxy-5-nitrophenyl)-6-phenyl-5-o-tolyl-3,4-dihydropyrimidin-2(1H)-one;
5-(4-chlorophenyl)-4-(3-ethoxy-4-hydroxy-5-nitrophenyl)-6-phenyl-3,4-dihydropyrimidin-2(1H)-one;
5-(2-chlorophenyl)-4-(3-ethoxy-4-hydroxy-5-nitrophenyl)-6-phenyl-3,4-dihydropyrimidin-2(1H)-one;
3-(4-(3-ethoxy-4-hydroxy-5-nitrophenyl)-2-oxo-6-phenyl-1,2,3,4-tetrahydropyrimidin-5-yl)benzonitrile;
5-(3,4-difluorophenyl)-4-(3-ethoxy-4-hydroxy-5-nitrophenyl)-6-phenyl-3,4-dihydropyrimidin-2(1H)-one;
4-(3-ethoxy-4-hydroxy-5-nitrophenyl)-6-(4-fluorophenyl)-5-phenyl-3,4-dihydropyrimidin-2(1H)-one;
6-(4-chlorophenyl)-4-(3-ethoxy-4-hydroxy-5-nitrophenyl)-5-phenyl-3,4-dihydropyrimidin-2(1H)-one;
6-(3-chlorophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-1,3-dimethyl-5,6-diphenyl-3,4-dihydropyrimidin-2(1H)-one;
6-(4-chloro-3-fluorophenyl)-4-(3-ethoxy-4-hydroxy-5-nitrophenyl)-5-phenyl-3,4-dihydropyrimidin-2(1H)-one;
6-(3-chloro-4-fluorophenyl)-4-(3-ethoxy-4-hydroxy-5-nitrophenyl)-5-phenyl-3,4-dihydropyrimidin-2(1H)-one;
6-(3,4-difluorophenyl)-4-(3-ethoxy-4-hydroxy-5-nitrophenyl)-5-phenyl-3,4-dihydropyrimidin-2(1H)-one;
6-(3,5-difluorophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(furan-3-yl)-5-phenyl-3,4-dihydropyrimidin-2(1H)-one;
4-(3-ethoxy-4-hydroxy-5-nitrophenyl)-6-(2-fluorophenyl)-5-phenyl-3,4-dihydropyrimidin-2(1H)-one;
4-(3-ethoxy-4-hydroxy-5-nitrophenyl)-3-methyl-5,6-diphenyl-3,4-dihydropyrimidin-2(1H)-one;
4-(3-ethoxy-5-fluoro-4-hydroxyphenyl)-5,6-diphenyl-3,4-dihydropyrimidin-2(1H)-one;
4-(3-ethoxy-4-hydroxy-5-nitrophenyl)-5-phenyl-6-(pyridin-3-yl)-3,4-dihydropyrimidin-2(1H)-one;
(R)-4-(3-ethoxy-4-hydroxy-5-nitrophenyl)-5-phenyl-6-(pyridin-3-yl)-3,4-dihydropyrimidin-2(1H)-one;
3-ethoxy-2-hydroxy-5-(2-oxo-5,6-diphenyl-1,2,3,4-tetrahydropyrimidin-4-yl)benzonitrile;
7-ethoxy-5-(2-oxo-5,6-diphenyl-1,2,3,4-tetrahydropyrimidin-4-yl)benzo[d]oxazol-2(3H)-one;
4-(3-ethoxy-4-hydroxy-5-nitrophenyl)-5-phenyl-6-(thiophen-2-yl)-3,4-dihydropyrimidin-2(1H)-one;
4-(3-ethoxy-4-hydroxy-5-nitrophenyl)-5-phenyl-6-(thiophen-3-yl)-3,4-dihydropyrimidin-2(1H)-one;
2-hydroxy-3-(2-oxo-5,6-diphenyl-1,2,3,4-tetrahydropyrimidin-4-yl)benzonitrile;
4-(4-hydroxy-3-nitrophenyl)-5,6-diphenyl-3,4-dihydropyrimidin-2(1H)-one;
4-(3-bromo-5-ethoxy-4-hydroxyphenyl)-5,6-diphenyl-3,4-dihydropyrimidin-2(1H)-one;
4-(3-ethoxy-4-hydroxy-5-nitrophenyl)-5-phenyl-6-(4-(trifluoromethyl)phenyl)-3,4-dihydropyrimidin-2(1H)-one;
4-(3-ethoxy-4-hydroxy-5-nitrophenyl)-5-(3-fluorophenyl)-6-phenyl-3,4-dihydropyrimidin-2(1H)-one;
4-(3-ethoxy-4-hydroxy-5-nitrophenyl)-6-(pyridin-3-yl)-5-(thiophen-3-yl)-3,4-dihydropyrimidin-2(1H)-one;
4-(3-ethoxy-4-hydroxy-5-nitrophenyl)-6-(1-methyl-1H-pyrazol-4-yl)-5-(thiophen-3-yl)-3,4-dihydropyrimidin-2(1H)-one;
4-(3-ethoxy-4-hydroxy-5-nitrophenyl)-6-(1-methyl-1H-pyrazol-3-yl)-5-(thiophen-3-yl)-3,4-dihydropyrimidin-2(1H)-one;
4-(3-chloro-4-hydroxy-5-nitrophenyl)-5,6-diphenyl-3,4-dihydropyrimidin-2(1H)-one;
4-(3-ethoxy-4-hydroxy-5-nitrophenyl)-5-(3-ethylphenyl)-6-phenyl-3,4-dihydropyrimidin-2(1H)-one;
4-ethoxy-6-(2-oxo-5,6-diphenyl-1,2,3,4-tetrahydropyrimidin-4-yl)benzo[d]oxazol-2(3H)-one;
4-(4-hydroxy-3-(2-methoxyethoxy)-5-nitrophenyl)-5,6-diphenyl-3,4-dihydropyrimidin-2(1H)-one;

6-cyclopentyl-4-(3-ethoxy-4-hydroxy-5-nitrophenyl)-5-phenyl-3,4-dihydropyrimidin-2(1H)-one; and 5-cyclohexyl-4-(3-ethoxy-4-hydroxy-5-nitrophenyl)-6-phenyl-3,4-dihydropyrimidin-2(1H)-one, or a pharmaceutically acceptable salt thereof.

10. The method of claim 1 wherein the compound is both an NK3 receptor antagonist and a GSNOR inhibitor.

* * * * *